(12) United States Patent
Shoshtaev et al.

(10) Patent No.: US 11,123,110 B2
(45) Date of Patent: Sep. 21, 2021

(54) POSTERIOR CERVICAL FIXATION SYSTEM

(71) Applicant: NuVasive Inc., San Diego, CA (US)

(72) Inventors: Eugene Shoshtaev, Del Mar, CA (US); Shaeffer Bannigan, San Diego, CA (US); Michael Brotman, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 136 days.

(21) Appl. No.: 16/453,631

(22) Filed: Jun. 26, 2019

(65) Prior Publication Data
US 2019/0314061 A1    Oct. 17, 2019

Related U.S. Application Data

(63) Continuation of application No. 15/936,107, filed on Mar. 26, 2018, now Pat. No. 10,368,918, which is a (Continued)

(51) Int. Cl.
*A61B 17/70* (2006.01)
*A61B 17/80* (2006.01)

(52) U.S. Cl.
CPC ........ *A61B 17/7052* (2013.01); *A61B 17/705* (2013.01); *A61B 17/7013* (2013.01); (Continued)

(58) Field of Classification Search
CPC ................ A61B 17/70; A61B 17/7049–7052
See application file for complete search history.

(56) References Cited

U.S. PATENT DOCUMENTS
| | | | |
|---|---|---|---|
| 929,067 A | 7/1909 | Williamson |
| 1,365,532 A | 1/1921 | Mountain |

(Continued)

FOREIGN PATENT DOCUMENTS
| AU | 723894 | 12/1998 |
|---|---|---|
| BR | PI08011303 | 6/2011 |

(Continued)

OTHER PUBLICATIONS

Beadling, "Harrington put the steel in spinal fixation", Orthopedics Today, (Jun. 2000), 6 pgs.

(Continued)

*Primary Examiner* — Eduardo C Robert
*Assistant Examiner* — Michelle C Eckman
(74) *Attorney, Agent, or Firm* — Hoffman Warnick LLC

(57) ABSTRACT

A posterior cervical fixation system including an occipital plate member, a cross connector, a pair of elongated spinal rods and a plurality of polyaxial screws. The occipital plate member configured for fixing to an occipital bone comprises an aperture to receive a bone anchor member to secure the occipital plate member to the occipital bone and at least one rod clamping element dimensioned to receive at least one spinal rod. The cross connector secures the pair of elongated spinal rods to vertebral bodies. The cross connector includes a pair of collet connectors and a cross bar that is configured to secure the pair of elongated spinal rods in a desired distance. Each polyaxial screw has an anchor head associated with a fastening member. The pair of elongated spinal rods is configured to extend along the vertebral bodies between the occipital plate member and at least one of the polyaxial screws.

18 Claims, 32 Drawing Sheets

Related U.S. Application Data continuation of application No. 15/182,414, filed on Jun. 14, 2016, now Pat. No. 9,956,009, which is a continuation of application No. 13/410,213, filed on Mar. 1, 2012, now Pat. No. 9,387,013.

(60) Provisional application No. 61/555,474, filed on Nov. 3, 2011, provisional application No. 61/450,130, filed on Mar. 8, 2011, provisional application No. 61/447,702, filed on Mar. 1, 2011.

(52) U.S. Cl.
CPC ...... *A61B 17/7037* (2013.01); *A61B 17/7049* (2013.01); *A61B 17/7055* (2013.01); *A61B 17/7056* (2013.01); *A61B 17/7064* (2013.01); *A61B 17/7082* (2013.01); *A61B 17/8061* (2013.01)

(56) References Cited

U.S. PATENT DOCUMENTS

| | | |
|---|---|---|
| 1,841,647 A | 1/1932 | Smith |
| 2,077,844 A | 4/1937 | Leighton |
| 3,367,326 A | 2/1968 | Frazier |
| 3,610,092 A | 10/1971 | Miller |
| 3,816,854 A | 6/1974 | Schlein |
| 4,361,141 A | 11/1982 | Tanner |
| 4,414,966 A | 11/1983 | Stednitz |
| 4,433,677 A | 2/1984 | Ulrich |
| 4,483,334 A | 11/1984 | Murray |
| 4,484,570 A | 11/1984 | Sutter |
| 4,537,185 A | 8/1985 | Stednitz |
| 4,569,338 A | 2/1986 | Edwards |
| 4,577,837 A | 3/1986 | Berg |
| 4,641,636 A | 2/1987 | Cotrel |
| 4,648,388 A | 3/1987 | Steffee |
| 4,771,767 A | 9/1988 | Steffee |
| 4,805,602 A | 2/1989 | Puno |
| 4,946,458 A | 8/1990 | Harms |
| 4,998,936 A | 3/1991 | Mehdian |
| 5,002,542 A | 3/1991 | Frigg |
| 5,005,562 A | 4/1991 | Cotrel |
| 5,024,213 A | 6/1991 | Asher |
| 5,034,011 A | 7/1991 | Howland |
| 5,042,982 A | 8/1991 | Harms |
| 5,047,029 A | 9/1991 | Aebi |
| 5,084,049 A | 1/1992 | Asher |
| 5,092,866 A | 3/1992 | Breard |
| 5,092,867 A | 3/1992 | Harms |
| 5,092,893 A | 3/1992 | Smith |
| 5,129,388 A | 7/1992 | Vignaud |
| 5,154,718 A | 10/1992 | Cozad |
| 5,176,680 A | 1/1993 | Vignaud |
| 5,196,013 A | 3/1993 | Harms |
| 5,207,678 A | 5/1993 | Harms |
| 5,209,752 A | 5/1993 | Ashman |
| 5,217,461 A | 6/1993 | Asher |
| 5,234,431 A | 8/1993 | Keller |
| 5,261,907 A | 11/1993 | Sacriste |
| 5,275,600 A | 1/1994 | Allard |
| 5,288,161 A | 2/1994 | Graves |
| 5,312,405 A | 5/1994 | Korotko |
| 5,318,388 A | 6/1994 | Papadopoulos |
| 5,330,473 A | 7/1994 | Howland |
| 5,332,330 A | 7/1994 | Kaneko |
| 5,360,429 A | 11/1994 | Jeanson |
| 5,375,823 A | 12/1994 | Navas |
| 5,380,323 A | 1/1995 | Howland |
| 5,387,213 A | 2/1995 | Breard |
| 5,397,363 A | 3/1995 | Gelbard |
| 5,403,314 A | 4/1995 | Currier |
| 5,437,669 A | 8/1995 | Yuan et al. |
| 5,437,671 A | 8/1995 | Lozier et al. |
| 5,443,467 A | 8/1995 | Biedermann |
| 5,466,237 A | 11/1995 | Byrd |
| 5,474,551 A | 12/1995 | Finn et al. |
| 5,474,555 A | 12/1995 | Puno |
| 5,476,464 A | 12/1995 | Metz-Stavenhagen |
| 5,478,340 A | 12/1995 | Kluger |
| 5,480,401 A | 1/1996 | Navas |
| 5,498,263 A | 3/1996 | Dinello |
| 5,501,684 A | 3/1996 | Schlapfer |
| 5,505,731 A | 4/1996 | Tornier |
| 5,507,745 A | 4/1996 | Logroscino |
| 5,522,816 A | 6/1996 | Dinello |
| 5,536,268 A | 7/1996 | Griss |
| 5,540,688 A | 7/1996 | Navas |
| 5,542,946 A | 8/1996 | Logroscino |
| 5,545,163 A | 8/1996 | Miller |
| 5,545,164 A | 8/1996 | Howland |
| 5,545,166 A | 8/1996 | Howland |
| 5,549,608 A | 8/1996 | Errico |
| 5,558,674 A | 9/1996 | Heggeness |
| 5,562,661 A | 10/1996 | Yoshimi |
| 5,569,246 A | 10/1996 | Ojima |
| 5,575,791 A | 11/1996 | Lin |
| 5,584,831 A | 12/1996 | Mckay |
| 5,593,408 A | 1/1997 | Gayet |
| 5,601,554 A | 2/1997 | Howland |
| 5,607,425 A | 3/1997 | Rogozinski |
| 5,609,593 A | 3/1997 | Errico |
| 5,624,442 A | 4/1997 | Mellinger |
| 5,630,816 A | 5/1997 | Kambin |
| 5,643,264 A | 7/1997 | Sherman |
| 5,645,544 A | 7/1997 | Tai |
| 5,653,708 A | 8/1997 | Howland |
| 5,665,122 A | 9/1997 | Kambin |
| 5,667,508 A | 9/1997 | Errico |
| 5,669,910 A | 9/1997 | Korhonen |
| 5,669,911 A | 9/1997 | Errico |
| 5,672,176 A | 9/1997 | Harms |
| 5,676,665 A | 10/1997 | Bryan |
| 5,676,703 A | 10/1997 | Gelbard |
| 5,681,311 A | 10/1997 | Foley |
| 5,681,319 A | 10/1997 | Biedermann |
| 5,688,272 A | 11/1997 | Montague |
| 5,688,275 A | 11/1997 | Koros et al. |
| 5,690,630 A | 11/1997 | Errico |
| 5,693,053 A | 12/1997 | Estes |
| 5,697,929 A | 12/1997 | Mellinger |
| 5,702,393 A | 12/1997 | Pfaifer |
| 5,704,936 A | 1/1998 | Mazel |
| 5,714,255 A | 2/1998 | Yeh |
| 5,716,355 A | 2/1998 | Jackson |
| 5,725,527 A | 3/1998 | Biedermann |
| 5,728,097 A | 3/1998 | Mathews |
| 5,728,098 A | 3/1998 | Sherman |
| 5,735,851 A | 4/1998 | Errico |
| 5,735,852 A | 4/1998 | Amrein |
| 5,741,255 A | 4/1998 | Glascott |
| 5,752,957 A | 5/1998 | Ralph |
| 5,776,135 A | 7/1998 | Errico |
| 5,782,831 A | 7/1998 | Sherman |
| 5,800,435 A | 9/1998 | Errico |
| 5,810,818 A | 9/1998 | Errico |
| 5,816,633 A | 10/1998 | Odom |
| 5,863,293 A | 1/1999 | Richelsoph |
| 5,873,878 A | 2/1999 | Harms |
| 5,879,350 A | 3/1999 | Sherman |
| 5,885,286 A | 3/1999 | Sherman |
| 5,891,145 A | 4/1999 | Morrison |
| 5,928,232 A | 7/1999 | Howland |
| 5,928,237 A | 7/1999 | Farris |
| 5,938,663 A | 8/1999 | Petreto |
| 5,944,719 A | 8/1999 | Leban |
| 5,944,720 A | 8/1999 | Lipton |
| 5,947,966 A | 9/1999 | Drewry |
| 5,951,555 A | 9/1999 | Rehak |
| 5,954,722 A | 9/1999 | Bono |
| 5,954,725 A | 9/1999 | Sherman |
| 5,961,516 A | 10/1999 | Graf |
| 5,964,769 A | 10/1999 | Wagner |
| 5,976,135 A | 11/1999 | Sherman |

(56) References Cited

U.S. PATENT DOCUMENTS

| | | |
|---|---|---|
| 5,980,521 A | 11/1999 | Montague |
| 5,980,523 A | 11/1999 | Jackson |
| 6,004,322 A | 12/1999 | Bernstein |
| 6,004,349 A | 12/1999 | Jackson |
| 6,030,389 A | 2/2000 | Wagner |
| 6,063,089 A | 5/2000 | Errico |
| 6,063,090 A | 5/2000 | Schlapfer |
| 6,074,391 A | 6/2000 | Metz-Stavenhagen |
| 6,083,226 A | 7/2000 | Fiz |
| 6,106,526 A | 8/2000 | Harms |
| 6,113,600 A | 9/2000 | Drummond |
| 6,113,601 A | 9/2000 | Tatar |
| 6,123,706 A | 9/2000 | Lange |
| 6,132,432 A | 10/2000 | Richelsoph |
| 6,136,003 A | 10/2000 | Drummond |
| 6,139,548 A | 10/2000 | Errico |
| 6,146,382 A | 11/2000 | Hurlbert |
| 6,171,311 B1 | 1/2001 | Richelsoph |
| 6,174,110 B1 | 1/2001 | Papadopoulos |
| 6,179,838 B1 | 1/2001 | Fiz |
| 6,183,473 B1 | 2/2001 | Ashman |
| 6,187,005 B1 | 2/2001 | Brace |
| 6,190,388 B1 | 2/2001 | Michelson |
| 6,210,413 B1 | 4/2001 | Sherman |
| 6,217,578 B1 | 4/2001 | Crozet |
| 6,224,596 B1 | 5/2001 | Jackson |
| 6,224,598 B1 | 5/2001 | Jackson |
| 6,231,575 B1 | 5/2001 | Krag |
| 6,234,705 B1 | 5/2001 | Troxell |
| 6,235,033 B1 | 5/2001 | Brace |
| 6,238,396 B1 | 5/2001 | Lombardo |
| 6,241,730 B1 | 6/2001 | Alby |
| 6,248,105 B1 | 6/2001 | Schläpfer |
| 6,251,112 B1 | 6/2001 | Jackson |
| 6,254,532 B1 | 7/2001 | Paolitto |
| 6,258,090 B1 | 7/2001 | Jackson |
| 6,261,288 B1 | 7/2001 | Jackson |
| 6,261,291 B1 | 7/2001 | Talaber |
| 6,264,658 B1 | 7/2001 | Lee |
| 6,267,765 B1 | 7/2001 | Taylor |
| 6,273,914 B1 | 8/2001 | Papas |
| 6,280,422 B1 | 8/2001 | Sanchez-Browning |
| 6,280,442 B1 | 8/2001 | Barker |
| 6,280,445 B1 | 8/2001 | Johnson |
| 6,283,967 B1 | 9/2001 | Kumar |
| 6,296,644 B1 | 10/2001 | Saurat |
| 6,306,137 B2 | 10/2001 | Troxell |
| 6,325,802 B1 | 12/2001 | Frigg |
| 6,328,740 B1 | 12/2001 | Richelsoph |
| 6,328,741 B1 | 12/2001 | Richelsoph |
| 6,379,354 B1 | 4/2002 | Rogozinski |
| 6,402,749 B1 | 6/2002 | Ashman |
| 6,402,751 B1 | 6/2002 | Hoeck |
| 6,413,258 B1 | 7/2002 | Bernhardt |
| 6,454,773 B1 | 9/2002 | Sherman |
| 6,471,703 B1 | 10/2002 | Ashman |
| 6,482,207 B1 | 11/2002 | Errico |
| 6,485,491 B1 | 11/2002 | Farris |
| 6,485,494 B1 | 11/2002 | Haider |
| 6,488,681 B2 | 12/2002 | Martin |
| 6,520,962 B1 | 2/2003 | Taylor |
| 6,524,310 B1 | 2/2003 | Lombardo |
| 6,524,315 B1 | 2/2003 | Selvitelli |
| 6,547,790 B2 | 4/2003 | Harkey |
| 6,551,318 B1 | 4/2003 | Stahurski |
| 6,554,832 B2 | 4/2003 | Shluzas |
| 6,554,834 B1 | 4/2003 | Crozet |
| 6,565,569 B1 | 5/2003 | Assaker et al. |
| 6,575,975 B2 | 6/2003 | Brace |
| 6,602,253 B2 | 8/2003 | Usher |
| 6,613,051 B1 | 9/2003 | Luk |
| 6,616,668 B2 | 9/2003 | Altarac |
| 6,623,485 B2 | 9/2003 | Doubler |
| 6,626,904 B1 | 9/2003 | Jammet |
| 6,626,906 B1 | 9/2003 | Young |
| 6,641,583 B2 | 11/2003 | Shluzas |
| 6,648,887 B2 | 11/2003 | Ashman |
| 6,660,004 B2 | 12/2003 | Barker |
| 6,685,705 B1 | 2/2004 | Taylor |
| 6,699,248 B2 | 3/2004 | Jackson |
| 6,709,435 B2 | 3/2004 | Lin |
| 6,716,214 B1 | 4/2004 | Jackson |
| 6,719,759 B2 | 4/2004 | Wagner |
| 6,736,817 B2 | 5/2004 | Troxell |
| 6,736,820 B2 | 5/2004 | Biedermann |
| 6,752,807 B2 | 6/2004 | Lin |
| 6,755,830 B2 | 6/2004 | Minfelde |
| 6,761,721 B2 | 7/2004 | Burgess |
| 6,783,526 B1 | 8/2004 | Lin |
| 6,802,844 B2 | 10/2004 | Ferree |
| 6,835,196 B2 | 12/2004 | Biedermann |
| 6,837,889 B2 | 1/2005 | Shluzas |
| 6,858,030 B2 | 2/2005 | Martin |
| 6,872,208 B1 | 3/2005 | Mcbride |
| 6,872,209 B2 | 3/2005 | Morrison |
| 6,875,211 B2 | 4/2005 | Nichols |
| 6,887,241 B1 | 5/2005 | Mcbride |
| 6,890,334 B2 | 5/2005 | Brace |
| 6,899,714 B2 | 5/2005 | Vaughan |
| 6,902,565 B2 | 6/2005 | Berger |
| 6,916,319 B2 * | 7/2005 | Munting ............ A61B 17/7043 606/250 |
| 6,958,066 B2 | 10/2005 | Richelsoph |
| 6,960,212 B2 | 11/2005 | Richelsoph |
| 6,964,666 B2 | 11/2005 | Jackson |
| 6,974,460 B2 | 12/2005 | Carbone |
| 7,022,122 B2 | 4/2006 | Amrein |
| 7,029,474 B2 | 4/2006 | Richelsoph |
| 7,066,938 B2 | 6/2006 | Slivka |
| 7,066,939 B2 | 6/2006 | Taylor |
| RE39,235 E | 8/2006 | Shuler |
| 7,083,621 B2 | 8/2006 | Shaolian |
| 7,083,622 B2 | 8/2006 | Simonson |
| 7,087,057 B2 | 8/2006 | Konieczynski |
| 7,104,992 B2 * | 9/2006 | Bailey ................ A61B 17/7037 606/256 |
| 7,104,993 B2 | 9/2006 | Baynham |
| 7,122,036 B2 | 10/2006 | Van Acker |
| 7,137,986 B2 | 11/2006 | Troxell |
| 7,160,301 B2 | 1/2007 | Cordaro |
| 7,163,539 B2 | 1/2007 | Abdelgany |
| 7,179,261 B2 | 2/2007 | Sicvol |
| 7,186,255 B2 | 3/2007 | Baynham |
| 7,204,853 B2 | 4/2007 | Gordon |
| 7,211,087 B2 | 5/2007 | Young |
| 7,223,268 B2 | 5/2007 | Biedermann |
| 7,232,441 B2 | 6/2007 | Altarac |
| 7,250,052 B2 | 7/2007 | Landry |
| 7,264,621 B2 | 9/2007 | Coates |
| 7,303,563 B2 | 12/2007 | Poyner |
| 7,377,923 B2 | 5/2008 | Purcell |
| 7,406,775 B2 | 8/2008 | Funk |
| 7,476,239 B2 | 1/2009 | Jackson |
| 7,481,827 B2 | 1/2009 | Ryan et al. |
| 7,530,992 B2 | 5/2009 | Biedermann |
| 7,618,443 B2 | 11/2009 | Abdou |
| 7,621,942 B2 | 11/2009 | Piehl |
| 7,625,033 B2 | 12/2009 | Michelau |
| 7,628,799 B2 | 12/2009 | Richelsoph et al. |
| 7,635,380 B2 | 12/2009 | Zucherman |
| 7,645,294 B2 | 1/2010 | Kalfas et al. |
| 7,678,112 B2 | 3/2010 | Rezach |
| 7,678,137 B2 | 3/2010 | Butler |
| 7,695,500 B2 | 4/2010 | Markworth |
| 7,699,873 B2 | 4/2010 | Stevenson |
| 7,722,648 B2 | 5/2010 | Drewry et al. |
| 7,727,261 B2 | 6/2010 | Barker |
| 7,731,736 B2 | 6/2010 | Guenther |
| 7,744,632 B2 | 6/2010 | Usher |
| 7,776,070 B2 | 8/2010 | Null |
| 7,785,354 B2 | 8/2010 | Biedermann |
| 7,794,478 B2 | 9/2010 | Nilsson |
| 7,799,054 B2 | 9/2010 | Kwak et al. |
| 7,803,174 B2 | 9/2010 | Denis et al. |

(56) References Cited

U.S. PATENT DOCUMENTS

| | | |
|---|---|---|
| 7,811,310 B2 | 10/2010 | Baker et al. |
| 7,819,902 B2 | 10/2010 | Abdelgany |
| 7,857,834 B2 | 12/2010 | Boschert |
| 7,862,588 B2 | 1/2011 | Abdou |
| 7,901,433 B2 | 3/2011 | Forton |
| 7,909,830 B2 | 3/2011 | Frigg |
| 7,914,558 B2 | 3/2011 | Landry |
| 7,947,065 B2 | 5/2011 | Hammill |
| 7,955,358 B2 | 6/2011 | Albert |
| 7,955,364 B2 | 6/2011 | Ziolo |
| 7,985,242 B2 | 7/2011 | Forton |
| 8,002,806 B2 | 8/2011 | Justis |
| 8,007,499 B2 | 8/2011 | Piehl |
| 8,012,177 B2 | 9/2011 | Jackson |
| 8,012,181 B2 | 9/2011 | Winslow |
| 8,021,397 B2 | 9/2011 | Farris |
| 8,021,398 B2 | 9/2011 | Sweeney |
| 8,034,084 B2 | 10/2011 | Landry |
| 8,043,341 B2 | 10/2011 | Zhao |
| 8,062,339 B2 | 11/2011 | Hammer |
| 8,100,946 B2 | 1/2012 | Strausbaugh |
| 8,147,527 B2 | 4/2012 | Hoffman |
| 8,162,990 B2 | 4/2012 | Potash |
| 8,167,908 B2 | 5/2012 | Ely et al. |
| 8,167,915 B2 | 5/2012 | Ferree |
| 8,172,847 B2 | 5/2012 | Dziedzic |
| 8,187,277 B2 | 5/2012 | Paul |
| 8,197,515 B2 | 6/2012 | Levy et al. |
| 8,221,472 B2 | 7/2012 | Peterson |
| 8,226,695 B2 | 7/2012 | Moore |
| 8,241,341 B2 | 8/2012 | Walker |
| 8,246,662 B2 | 8/2012 | Lemoine |
| 8,277,490 B2 | 10/2012 | Freeman |
| 8,287,542 B2 | 10/2012 | Wolter |
| 8,308,774 B2 | 11/2012 | Hoffman |
| 8,328,853 B2 | 12/2012 | Ibrahim |
| 8,337,496 B2 | 12/2012 | Piehl |
| 8,348,981 B2 | 1/2013 | Cheema |
| 8,430,916 B1 | 4/2013 | Winslow et al. |
| 8,480,712 B1 | 7/2013 | Samuel et al. |
| 8,506,567 B2 | 8/2013 | Ziemek et al. |
| 8,506,601 B2 | 8/2013 | Gephart |
| 8,545,500 B2 | 10/2013 | Babat |
| 8,585,741 B2 | 11/2013 | Gabelberger et al. |
| 8,864,798 B2 | 10/2014 | Weiman et al. |
| 9,023,087 B2 | 5/2015 | Frankel et al. |
| 9,198,696 B1 | 12/2015 | Bannigan et al. |
| 9,247,964 B1 * | 2/2016 | Shoshtaev ............. A61B 17/70 |
| 9,629,663 B2 * | 4/2017 | Ludwig ............. A61B 17/7007 |
| 9,956,009 B1 * | 5/2018 | Shoshtaev .......... A61B 17/7055 |
| 2001/0034521 A1 | 10/2001 | Bailey |
| 2002/0049446 A1 | 5/2002 | Harkey |
| 2002/0052603 A1 | 5/2002 | Nichols |
| 2002/0058942 A1 | 5/2002 | Biedermann |
| 2002/0120268 A1 | 8/2002 | Berger |
| 2002/0143330 A1 | 10/2002 | Shluzas |
| 2002/0169448 A1 | 11/2002 | Vanacker |
| 2002/0173789 A1 | 11/2002 | Howland |
| 2003/0023244 A1 | 1/2003 | Richelsoph |
| 2003/0023564 A1 | 1/2003 | Padhye |
| 2003/0028191 A1 | 2/2003 | Shluzas |
| 2003/0045874 A1 | 3/2003 | Thomas |
| 2003/0045878 A1 | 3/2003 | Petit |
| 2003/0100896 A1 | 5/2003 | Biedermann |
| 2003/0114853 A1 | 6/2003 | Burgess et al. |
| 2003/0144665 A1 | 7/2003 | Munting |
| 2003/0149432 A1 | 8/2003 | Frigg |
| 2003/0153913 A1 | 8/2003 | Altarac |
| 2003/0153917 A1 | 8/2003 | Richelsoph |
| 2003/0163133 A1 | 8/2003 | Altarac |
| 2003/0187435 A1 | 10/2003 | Lin |
| 2003/0212398 A1 | 11/2003 | Jackson |
| 2003/0225408 A1 | 12/2003 | Nichols |
| 2004/0087949 A1 | 5/2004 | Bono et al. |
| 2004/0116928 A1 | 6/2004 | Young |
| 2004/0138661 A1 | 7/2004 | Bailey |
| 2004/0138662 A1 | 7/2004 | Landry |
| 2004/0143265 A1 | 7/2004 | Landry |
| 2004/0147928 A1 | 7/2004 | Landry |
| 2004/0153070 A1 | 8/2004 | Barker |
| 2004/0153077 A1 | 8/2004 | Biedermann |
| 2004/0162558 A1 | 8/2004 | Hegde et al. |
| 2004/0172022 A1 | 9/2004 | Landry |
| 2004/0243126 A1 | 12/2004 | Carbone |
| 2004/0254574 A1 | 12/2004 | Morrison et al. |
| 2004/0260284 A1 | 12/2004 | Parker |
| 2004/0260285 A1 | 12/2004 | Steib et al. |
| 2004/0260287 A1 | 12/2004 | Ferree |
| 2005/0010217 A1 | 1/2005 | Dalton |
| 2005/0070901 A1 | 3/2005 | David |
| 2005/0080415 A1 | 4/2005 | Keyer |
| 2005/0080416 A1 | 4/2005 | Ryan |
| 2005/0080417 A1 | 4/2005 | Alexis |
| 2005/0080420 A1 | 4/2005 | Farris |
| 2005/0085813 A1 | 4/2005 | Spitler |
| 2005/0090821 A1 | 4/2005 | Berrevoets |
| 2005/0096654 A1 | 5/2005 | Lin |
| 2005/0101954 A1 | 5/2005 | Simonson |
| 2005/0113927 A1 | 5/2005 | Malek |
| 2005/0124994 A1 | 6/2005 | Berger |
| 2005/0137594 A1 | 6/2005 | Doubler |
| 2005/0154391 A1 | 7/2005 | Doherty |
| 2005/0154393 A1 | 7/2005 | Doherty |
| 2005/0182409 A1 | 8/2005 | Callahan |
| 2005/0192572 A1 | 9/2005 | Abdelgany |
| 2005/0228326 A1 | 10/2005 | Kalfas |
| 2005/0228376 A1 | 10/2005 | Boomer |
| 2005/0228382 A1 | 10/2005 | Richelsoph |
| 2005/0240181 A1 | 10/2005 | Boomer |
| 2005/0240185 A1 | 10/2005 | Boomer |
| 2005/0251141 A1 | 11/2005 | Frigg |
| 2005/0261690 A1 | 11/2005 | Binder |
| 2005/0277923 A1 | 12/2005 | Sweeney |
| 2005/0277927 A1 | 12/2005 | Guenther |
| 2005/0277928 A1 | 12/2005 | Boschert |
| 2005/0283153 A1 | 12/2005 | Poyner |
| 2005/0288669 A1 | 12/2005 | Abdou |
| 2005/0288670 A1 | 12/2005 | Panjabi |
| 2006/0004363 A1 | 1/2006 | Brockmeyer |
| 2006/0009766 A1 | 1/2006 | Lee et al. |
| 2006/0025769 A1 | 2/2006 | Dick et al. |
| 2006/0025771 A1 | 2/2006 | Jackson |
| 2006/0036244 A1 | 2/2006 | Spitler |
| 2006/0036252 A1 | 2/2006 | Baynham |
| 2006/0052783 A1 | 3/2006 | Dant |
| 2006/0052786 A1 | 3/2006 | Dant |
| 2006/0058787 A1 | 3/2006 | David |
| 2006/0058789 A1 | 3/2006 | Kim |
| 2006/0060823 A1 | 3/2006 | Cooke |
| 2006/0064091 A1 | 3/2006 | Ludwig |
| 2006/0064093 A1 | 3/2006 | Thramann |
| 2006/0084978 A1 | 4/2006 | Mokhtar |
| 2006/0084979 A1 | 4/2006 | Jackson |
| 2006/0084993 A1 | 4/2006 | Khoo |
| 2006/0084995 A1 | 4/2006 | Biedermann |
| 2006/0089651 A1 | 4/2006 | Trudeau |
| 2006/0095035 A1 | 5/2006 | Jones |
| 2006/0095038 A1 | 5/2006 | Jackson |
| 2006/0100622 A1 | 5/2006 | Jackson |
| 2006/0111712 A1 | 5/2006 | Jackson |
| 2006/0111713 A1 | 5/2006 | Jackson |
| 2006/0111714 A1 | 5/2006 | Foley |
| 2006/0111715 A1 | 5/2006 | Jackson |
| 2006/0122604 A1 | 6/2006 | Gorhan |
| 2006/0142761 A1 | 6/2006 | Wagner |
| 2006/0149229 A1 | 7/2006 | Kwak |
| 2006/0149232 A1 | 7/2006 | Sasing |
| 2006/0149233 A1 | 7/2006 | Richelsoph |
| 2006/0149240 A1 | 7/2006 | Jackson |
| 2006/0155277 A1 | 7/2006 | Metz-Stavenhagen |
| 2006/0155283 A1 | 7/2006 | Doherty |
| 2006/0155284 A1 | 7/2006 | Doherty |
| 2006/0161153 A1 | 7/2006 | Hawkes |
| 2006/0167454 A1 | 7/2006 | Ludwig |

(56) References Cited

U.S. PATENT DOCUMENTS

| | | |
|---|---|---|
| 2006/0167455 A1 | 7/2006 | Clement et al. |
| 2006/0173454 A1 | 8/2006 | Spitler |
| 2006/0173456 A1 | 8/2006 | Hawkes |
| 2006/0179244 A1 | 8/2006 | Goodman |
| 2006/0200133 A1 | 9/2006 | Jackson |
| 2006/0200136 A1 | 9/2006 | Jackson |
| 2006/0217710 A1 | 9/2006 | Abdou |
| 2006/0217718 A1 | 9/2006 | Chervitz |
| 2006/0217723 A1 | 9/2006 | Suh |
| 2006/0217725 A1 | 9/2006 | Suh |
| 2006/0217735 A1 | 9/2006 | Macdonald |
| 2006/0229606 A1 | 10/2006 | Clement |
| 2006/0229610 A1 | 10/2006 | Piehl |
| 2006/0229616 A1 | 10/2006 | Albert et al. |
| 2006/0235393 A1 | 10/2006 | Bono |
| 2006/0241599 A1 | 10/2006 | Konieczynski |
| 2006/0241601 A1 | 10/2006 | Trautwein |
| 2006/0241603 A1 | 10/2006 | Jackson |
| 2006/0247624 A1 | 11/2006 | Banouskou |
| 2006/0247631 A1 | 11/2006 | Ahn |
| 2006/0264933 A1 | 11/2006 | Baker |
| 2006/0271045 A1 | 11/2006 | Hubbard |
| 2006/0271047 A1 | 11/2006 | Jackson |
| 2006/0271050 A1 | 11/2006 | Piza Vallespir |
| 2006/0276789 A1 | 12/2006 | Jackson |
| 2006/0276792 A1 | 12/2006 | Ensign |
| 2006/0282074 A1 | 12/2006 | Renaud |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2007/0016200 A1 | 1/2007 | Jackson |
| 2007/0032162 A1 | 2/2007 | Jackson |
| 2007/0049932 A1 | 3/2007 | Richelsoph |
| 2007/0049933 A1 | 3/2007 | Ahn |
| 2007/0055239 A1 | 3/2007 | Sweeney |
| 2007/0055240 A1 | 3/2007 | Matthis |
| 2007/0055241 A1 | 3/2007 | Matthis |
| 2007/0055244 A1 | 3/2007 | Jackson |
| 2007/0078460 A1 | 4/2007 | Frigg |
| 2007/0083201 A1 | 4/2007 | Jones |
| 2007/0088357 A1 | 4/2007 | Johnson |
| 2007/0093818 A1 | 4/2007 | Biedermann |
| 2007/0093827 A1 | 4/2007 | Warnick |
| 2007/0118121 A1 | 5/2007 | Purcell |
| 2007/0118123 A1 | 5/2007 | Strausbaugh |
| 2007/0123860 A1 | 5/2007 | Francis |
| 2007/0123862 A1 | 5/2007 | Warnick |
| 2007/0123869 A1 | 5/2007 | Chin |
| 2007/0123870 A1 | 5/2007 | Jeon |
| 2007/0149973 A1 | 6/2007 | Clement |
| 2007/0161987 A1 | 7/2007 | Capote et al. |
| 2007/0161988 A1 | 7/2007 | Drewry |
| 2007/0167946 A1 | 7/2007 | Triplett et al. |
| 2007/0167949 A1 | 7/2007 | Altarac |
| 2007/0173819 A1 | 7/2007 | Sandlin |
| 2007/0173825 A1 | 7/2007 | Sharifi-Mehr |
| 2007/0173829 A1 | 7/2007 | Drewry |
| 2007/0173833 A1 | 7/2007 | Butler |
| 2007/0213720 A1 | 9/2007 | Gordon |
| 2007/0213721 A1 | 9/2007 | Markworth |
| 2007/0213723 A1 | 9/2007 | Markworth |
| 2007/0233062 A1 | 10/2007 | Berry |
| 2007/0233090 A1 | 10/2007 | Naifeh |
| 2007/0233119 A1 | 10/2007 | Markworth |
| 2007/0250061 A1 | 10/2007 | Chin et al. |
| 2007/0265621 A1 | 11/2007 | Matthis |
| 2007/0270808 A1 | 11/2007 | Drewry |
| 2007/0270809 A1 | 11/2007 | Drewry |
| 2007/0270810 A1 | 11/2007 | Sanders |
| 2007/0270842 A1 | 11/2007 | Bankoski |
| 2007/0288009 A1 | 12/2007 | Brown |
| 2007/0299441 A1 | 12/2007 | Hoffman |
| 2008/0021454 A1 | 1/2008 | Chao |
| 2008/0021464 A1 | 1/2008 | Morin |
| 2008/0027436 A1 | 1/2008 | Cournoyer |
| 2008/0033434 A1 | 2/2008 | Boomer |
| 2008/0039844 A1 | 2/2008 | Jackson |
| 2008/0045955 A1 | 2/2008 | Berrevoets |
| 2008/0051780 A1 | 2/2008 | Vaidya |
| 2008/0051783 A1 | 2/2008 | Null |
| 2008/0071273 A1 | 3/2008 | Hawkes et al. |
| 2008/0077143 A1 | 3/2008 | Shluzas |
| 2008/0086124 A1 | 4/2008 | Forton |
| 2008/0091204 A1 | 4/2008 | Kuiper |
| 2008/0091205 A1 | 4/2008 | Kuiper et al. |
| 2008/0091213 A1 | 4/2008 | Jackson |
| 2008/0109039 A1 | 5/2008 | Michielli |
| 2008/0125781 A1 | 5/2008 | Hoffman |
| 2008/0132953 A1 | 6/2008 | Carbone |
| 2008/0140075 A1 | 6/2008 | Ensign |
| 2008/0147123 A1 | 6/2008 | Schermerhorn |
| 2008/0154277 A1 | 6/2008 | Machalk |
| 2008/0161859 A1 | 7/2008 | Nilsson |
| 2008/0161861 A1 | 7/2008 | Huebner |
| 2008/0167688 A1 | 7/2008 | Fauth et al. |
| 2008/0172093 A1 | 7/2008 | Nilsson |
| 2008/0177260 A1 | 7/2008 | Mckinley |
| 2008/0177313 A1 | 7/2008 | Lemoine et al. |
| 2008/0177314 A1 | 7/2008 | Lemoine |
| 2008/0177315 A1 | 7/2008 | Usher |
| 2008/0177323 A1 | 7/2008 | Null |
| 2008/0183214 A1 | 7/2008 | Copp |
| 2008/0208256 A1 | 8/2008 | Thramann |
| 2008/0221622 A1 | 9/2008 | Triplett et al. |
| 2008/0234755 A1 | 9/2008 | Cummins |
| 2008/0249576 A1 | 10/2008 | Hawkes |
| 2008/0255617 A1 | 10/2008 | Cho |
| 2008/0269742 A1 | 10/2008 | Levy |
| 2008/0294195 A1 | 11/2008 | Egli et al. |
| 2008/0306525 A1 | 12/2008 | Mitchell |
| 2008/0306534 A1 | 12/2008 | Winslow |
| 2008/0306535 A1 | 12/2008 | Winslow |
| 2008/0306540 A1 | 12/2008 | Mitchell |
| 2008/0306541 A1 | 12/2008 | Mitchell |
| 2008/0306542 A1 | 12/2008 | Mitchell |
| 2008/0312692 A1 | 12/2008 | Brennan |
| 2009/0005814 A1 | 1/2009 | Miller |
| 2009/0005815 A1 | 1/2009 | Ely |
| 2009/0018584 A1 | 1/2009 | Henderson, Sr. |
| 2009/0043338 A1 | 2/2009 | Laager |
| 2009/0062860 A1 | 3/2009 | Frasier |
| 2009/0071273 A1 | 3/2009 | Velasco |
| 2009/0082812 A1 | 3/2009 | Lewis |
| 2009/0082813 A1 | 3/2009 | Long |
| 2009/0125065 A1 | 5/2009 | Laager |
| 2009/0125067 A1 | 5/2009 | Mazzuca |
| 2009/0138044 A1 | 5/2009 | Bergeron |
| 2009/0157125 A1 | 6/2009 | Hoffman |
| 2009/0198280 A1 | 8/2009 | Spratt |
| 2009/0204155 A1 | 8/2009 | Aschmann |
| 2009/0216277 A1 | 8/2009 | Tornier |
| 2009/0264931 A1 | 10/2009 | Miller et al. |
| 2009/0270924 A1 | 10/2009 | Wing |
| 2009/0306721 A1 | 12/2009 | Kirschman |
| 2009/0318968 A1 | 12/2009 | Duggal |
| 2010/0010541 A1 | 1/2010 | Boomer |
| 2010/0094306 A1 | 4/2010 | Chang |
| 2010/0094345 A1* | 4/2010 | Saidha .............. A61B 17/7052 606/250 |
| 2010/0094346 A1 | 4/2010 | Matityahu |
| 2010/0094349 A1 | 4/2010 | Hammer |
| 2010/0094351 A1 | 4/2010 | Haggenmaker |
| 2010/0114177 A1 | 5/2010 | Piehl |
| 2010/0125299 A1 | 5/2010 | Paul |
| 2010/0145394 A1 | 6/2010 | Harvey |
| 2010/0160977 A1 | 6/2010 | Gephart |
| 2010/0160981 A1 | 6/2010 | Butler |
| 2010/0191289 A1 | 7/2010 | Ludwig |
| 2010/0198260 A1 | 8/2010 | Gabelberger |
| 2010/0204733 A1 | 8/2010 | Rathbun |
| 2010/0204735 A1 | 8/2010 | Gephart |
| 2010/0211100 A1 | 8/2010 | Mack |

(56) References Cited

U.S. PATENT DOCUMENTS

| | | |
|---|---|---|
| 2010/0222779 A1 | 9/2010 | Ziemek |
| 2010/0222825 A1 | 9/2010 | Paul |
| 2010/0234891 A1 | 9/2010 | Freeman |
| 2010/0268279 A1 | 10/2010 | Gabelberger |
| 2010/0324557 A1 | 12/2010 | Cheema |
| 2010/0324599 A1 | 12/2010 | Montello |
| 2011/0004250 A1 | 1/2011 | Uribe |
| 2011/0034957 A1 | 2/2011 | Biedermann |
| 2011/0046675 A1 | 2/2011 | Barrus |
| 2011/0066189 A2 | 3/2011 | Beidermann |
| 2011/0071569 A1 | 3/2011 | Black |
| 2011/0087288 A1 | 4/2011 | Stevenson |
| 2011/0098748 A1 | 4/2011 | Jangra |
| 2011/0106085 A1 | 5/2011 | Null |
| 2011/0106178 A1 | 5/2011 | Schwab |
| 2011/0125195 A1 | 5/2011 | Biedermann |
| 2011/0178559 A1 | 7/2011 | Barry |
| 2011/0184462 A1 | 7/2011 | Gil |
| 2011/0190824 A1 | 8/2011 | Gephart |
| 2011/0251645 A1 | 10/2011 | Black |
| 2011/0270314 A1 | 11/2011 | Mueller et al. |
| 2011/0319943 A1 | 12/2011 | Donahoe |
| 2012/0035659 A1 | 2/2012 | Barrus et al. |
| 2012/0035663 A1 | 2/2012 | Jackson |
| 2012/0039566 A1 | 2/2012 | Ruiz Cruz |
| 2012/0065686 A1 | 3/2012 | Black |
| 2012/0071926 A1 | 3/2012 | Jani |
| 2012/0078306 A1 | 3/2012 | Lynch |
| 2012/0095511 A1 | 4/2012 | Nihalani |
| 2012/0095512 A1 | 4/2012 | Nihalani |
| 2012/0101529 A1 | 4/2012 | Ludwig |
| 2012/0123477 A1 | 5/2012 | Landry |
| 2012/0130436 A1 | 5/2012 | Haskins |
| 2012/0226316 A1 | 9/2012 | Dant et al. |
| 2012/0226317 A1 | 9/2012 | Potash |
| 2012/0239090 A1 | 9/2012 | Abdou |
| 2012/0259369 A1 | 10/2012 | Hammer |
| 2012/0271360 A1 | 10/2012 | Moore |
| 2013/0023932 A1 | 1/2013 | Helgerson |
| 2013/0023939 A1 | 1/2013 | Pischl |
| 2013/0172934 A1 | 7/2013 | Walker et al. |
| 2013/0238033 A1 | 9/2013 | Black |
| 2013/0253516 A1 | 9/2013 | Mackall |
| 2013/0274808 A1 | 10/2013 | Larroque-Lahitette et al. |
| 2014/0088649 A1 | 3/2014 | Refai |
| 2014/0277156 A1 | 9/2014 | Hammer |
| 2016/0106470 A1 | 4/2016 | Refai |
| 2016/0374728 A1 | 12/2016 | Kim |
| 2017/0311986 A1 | 11/2017 | McNab et al. |

FOREIGN PATENT DOCUMENTS

| | | |
|---|---|---|
| CA | 2045502 | 5/1991 |
| DE | 3841008 | 6/1990 |
| DE | 9004960 | 8/1991 |
| DE | 19950075 | 4/2001 |
| DE | 10055888 | 4/2002 |
| DE | 102009060396 | 6/2011 |
| EP | 0283373 | 9/1988 |
| EP | 1743585 | 12/2007 |
| FR | 2624720 | 6/1989 |
| FR | 2687561 | 8/1993 |
| WO | WO-1995013754 | 5/1995 |
| WO | WO-1998032386 | 7/1998 |
| WO | WO-1998052482 | 11/1998 |
| WO | WO-2006025919 | 3/2006 |
| WO | WO-2006029373 | 3/2006 |
| WO | WO-2006096756 | 1/2007 |
| WO | WO-2007061960 | 5/2007 |
| WO | WO-2007084900 | 7/2007 |
| WO | WO-2007130007 | 11/2007 |
| WO | WO-2008013892 | 1/2008 |
| WO | WO-2008105643 | 9/2008 |
| WO | WO-2009012247 | 1/2009 |
| WO | WO-2009041923 | 4/2009 |
| WO | WO-2009055747 | 4/2009 |
| WO | WO-2010002409 | 1/2010 |
| WO | WO-2010045219 | 4/2010 |
| WO | WO-2011057178 | 5/2011 |
| WO | WO-2011088358 | 7/2011 |

OTHER PUBLICATIONS

Dipreta, "The Iliac Nail/Screw in a Modified Galveston Technique for Sacropelvic Fixation", *Am. Acad. of Ortho. Surg.*, $67^{th}$ mtg., PE184, (Mar. 19, 2000), 1 pg.

Ebrahim, "Posterior Lateral Mass Screw Fixation: Anatomic and Radiographic Considerations", *U.P.O.J.* vol. 12 (Spring 1999), 66-72.

Erickson, "Biomechanical Assessment of Conventional Unit Rod Fixation Versus a Unit Rod Pedicle Screw Construct", *Spine*, vol. 29, No. 12, (2004), 1314-1319.

Pham, "Upper cervical spine surgery in rheumatoid arthritis: retrospective study of 30 patients followed for two years or more after Cotrel-Dubousset instrumentation", *Joint Bone Spine*, 67 (2000), 434-440.

Sanders, "Treating, managing spinal deformity in young patients", Orthopedics Today (Jul. 2001), 12 pgs.

Spiegel, "Anterior instrumentation in the Treatment of Scolisosis" *U.P.O.J.*, vol. 11, (Spring. 1998), 19-26.

Synthes Spine, "The CerviFix System Including the StarLock Components," 2000, 16 pages.

Wood, "Torsional Rigidity of Scoliosis Constructs", *Spine*, vol. 25, No. 15, (2000), 1893-1898.

\* cited by examiner

POSTERIOR CERVICAL FIXATION SYSTEM

CROSS REFERENCES TO RELATED APPLICATIONS

This application is a continuation application of U.S. patent application Ser. No. 15/936,107 filed Mar. 26, 2018, which is a continuation of U.S. patent application Ser. No. 15/182,414, which is a continuation of U.S. patent application Ser. No. 13/410,213 filed Mar. 1, 2012, which claims the benefit of the filing date of U.S. Provisional Application No. 61/447,702 filed on Mar. 1, 2011, U.S. Provisional Application No. 61/450,130 filed on Mar. 8, 2011, and U.S. Provisional No. 61/555,474 filed on Nov. 3, 2011, the entire contents of which are incorporated herein by reference.

FIELD

The present embodiment relates in general to spinal fixation systems and, more particularly, to a posterior cervical fixation system configured for attachment to the posterior part of the human spine from the occipital portion of the human to cervical and/or thoracic vertebrae.

BACKGROUND

The spinal column is a bio-mechanical structure composed primarily of ligaments, muscles, bones, and connective tissue that forms a series of vertebral bodies stacked one atop the other and intervertebral discs between each vertebral body. The spinal column provides support to the body and provides for the transfer of the weight and the bending movements of the head, trunk and arms to the pelvis and legs; complex physiological motion between these parts; and protection of the spinal cord and the nerve roots.

Common spinal column disorders include degenerative disc disease, facet arthritis, and other conditions such as spondylolysis, spondylolisthesis, scoliosis, fractured vertebra, ruptured or slipped discs, tumors, or infections and other disorders caused by abnormalities, disease or trauma. Patients who suffer from one of more of these conditions often experience extreme pain, and can sustain permanent neurologic damage if the conditions are not treated appropriately.

The stabilization of the vertebra and the treatment for above described conditions is often aided by a surgically implanted fixation device which holds the vertebral bodies in proper alignment and reduces the patient's pain and prevents neurologic loss of function. Spinal fixation is a well-known and frequently used medical procedure. Spinal fixation systems are often surgically implanted into a patient to aid in the stabilization of a damaged spine or to aid in the correction of other spinal deformities. Existing systems often use a combination of rods, plates, pedicle screws, bone hooks locking screw assemblies and connectors for fixing the system to the affected vertebrae. The system components may be rigidly locked together in a variety of configurations to promote fusion for a wide variety of patient anatomies.

Posterior fusion and fixation may be the optimal approach for patients in whom the construct requires an extension to the upper cervical or thoracic spine, and to the occiput. Overall, posterior stabilization is generally preferred for posterior and circumferential cervical injuries. Several kinds of posterior fixation systems have been devised. Examples include sublaminar wiring with rod/plate fixation, laminar hook with rod fixation, and pedicle screw with a rod fixation system. However, the sublaminar wiring system has a restriction because the lower cervical laminae are smaller and weaker than upper thoracic vertebrae; and, laminar hooks are not preferred because they cannot be fixed in the narrow spinal canal. Alternatively, posterior screw fixation systems provide excellent stability and strength for patients without any external support.

Advancements in posterior cervical fixation have progressed from a wiring procedure to hook and plate-screw systems; and more recently to the versatile rod-screw system.

In some fixation systems, the plates are mounted to the skull with several small screws along the full length and width of the plate. As a result, the spinal rods must be bent in multiple planes away from the vertebrae in order to reach the occipital region. This bending of the rod may potentially weaken the overall assembly, and result in longer operations; and also makes it more difficult to reposition the elements of the stabilization system.

Therefore, there is a need for a posterior cervical fixation system that includes the easy installation of rods which would reduce the risk of implant failure and loss of alignment; and provide for easy adaptation for extension to the occiput or cervical/thoracic spine.

SUMMARY

The posterior cervical fixation system comprises a pair of elongated spinal rods, an occipital plate member, a cross connector and a plurality of polyaxial screws. The posterior cervical fixation system of the preferred embodiment is described herein for attachment to the posterior part of the human spine from the occiput to the cervical and/or thoracic vertebrae. The posterior cervical fixation system facilitates securing of an orthopedic rod to the spine/skull.

The occipital plate member is configured for fixing to an occipital bone. The occipital plate member includes at least one aperture, that receives at least one bone anchor member to secure the occipital plate member to the occipital bone and at least one rod clamping element that is dimensioned to receive the spinal rod. Each polyaxial screw includes an anchor head that is associated with a fastening member. The pair of elongated spinal rods includes a first elongated spinal rod and a second elongated spinal rod which is configured to extend along vertebral bodies between the occipital plate member and at least one polyaxial screw.

The cross connector secures the first and second elongated spinal rods to the vertebral bodies of the spine. The cross connector includes a pair of collet connectors and a cross bar which is configured to secure the first and second elongated spinal rods in desired distance. The fastening member of the polyaxial screw is inserted in the vertebral bodies by facing the anchor head upwards to receive the elongated spinal rods. The elongated spinal rods are effectively locked in the anchor head by connecting the cross connector in the anchor head.

One embodiment of the occipital plate member of the posterior cervical fixation system comprises an upper surface and a lower surface, in which the lower surface is configured to contact a portion of the occipital bone. The occipital plate member includes generally a flat main body portion having a first surface, a second surface and a centerline axis. Both first and second surfaces have a recessed portion and an opening and the centerline axis has a plurality of openings. The main body portion further includes a first end in which at least a portion of the first end extends away from the centerline axis and a second end in which at least a portion of the second end extends away from the centerline axis. The occipital plate member is fixed to the occipital bone by inserting a plurality of bone anchor members through the plurality of openings in the centerline axis and each opening on the first and second surfaces of the main body portion.

The openings on the first and second surfaces are fitted with a washer that interfaces with the occipital plate member and the bone anchor member. The occipital plate member further includes a first rotating housing having a lower portion and a hole adaptable to engage with the recessed portion and the opening of the first surface, a second rotating housing having a lower portion and a hole adaptable to engage with the recessed portion and the opening of the second surface.

The occipital plate member further includes a first rod clamping element and a second rod clamping element. The first rod clamping element is dimensioned to couple the occipital plate member to a first elongated spinal rod. Similarly, the second rod clamping element is dimensioned to couple the occipital plate member to a second elongated spinal rod. The first rod clamping element extends laterally from the first end of the main body portion and the second rod clamping element extends laterally from the second end of the main body portion. The first rod clamping element includes a first clamp portion having a rod receiving end and a hole extending therethrough in communication with the rod receiving end and a first body portion having a pin slot therethrough on a body of the first body portion. Similarly, the second rod clamping element includes a second clamp portion having a rod receiving end and a hole extending therethrough in communication with the rod receiving end and a second body portion having a pin slot therethrough on a body of the second body portion.

The occipital plate member further includes a plurality of pins that is coupled to the first and second rotating housings. The pin slots of the first and second rod clamping elements receive the pins and enable each of the rod clamping elements to rotate in medially and laterally within each of the rotating housings to achieve a collapsed state and an expanded state. The occipital plate member further includes a first locking element to lock the first elongated spinal rod within the rod receiving end of the first rod clamping element and a second locking element to lock the second elongated spinal rod within the rod receiving end of the second rod clamping element. The first and second locking elements comprise a set screw.

In order to achieve this locking interaction, the set screws threadedly engage the holes on the first and second clamp portions such that the set screws may be advanced toward the elongated spinal rods until a distal tip of the set screws contacts the elongated spinal rods. A first locking means engages the first rotating housing and the first rod clamping element to the main body portion and a second locking means engages the second rotating housing and the second rod clamping element to the main body portion. Specifically, both the locking means comprise a lock nut which is dimensioned to interlock the first and second rotating housings and the first and second rod clamping elements with the first and second surfaces of the main body portion. The first and second rod clamping elements have generally C-shaped rod-receiving ends to facilitate side loading of the elongated spinal rods.

Yet another embodiment of an occipital plate member is similar to the first embodiment discussed above, but the first and second rod clamping elements have a generally U-shaped rod-receiving ends with threaded side walls extending therethrough in communication with the rod receiving ends respectively, in which the rod receiving ends are dimensioned to face upward. Also, the first and second locking means is a locking screw which is positioned vertically offset from center of the rotating housings. The first and second locking means enables the locking of the first and second rod clamping elements and the first and second rotating housings in a desired position. The openings in the main body portion are angled such that the bone anchor members are guided into the occipital bone at an oblique angle to the transverse axis of the occipital plate member.

Still another embodiment of an occipital plate member is similar to the second embodiment discussed above, but the U-shaped rod-receiving ends with a threaded side walls extending therethrough in communication with the rod receiving ends is attached with rod receiving towers having threaded side walls extending therethrough in communication with the rod receiving towers.

The cross connector forming part of a posterior cervical fixation system includes a first connector, a second connector and a cross bar. The cross bar includes a first end that is surrounded with a first ball spring collar and a second end that is surrounded with a second ball spring collar. The first connector is configured to receive the first elongated spinal rod and is adaptable to directly attach with a first polyaxial screw. Similarly, the second connector is configured to receive a second elongated spinal rod and adaptable to directly attach with a second polyaxial screw.

The first connector includes a first collet head having a recess to receive an anchor head of the first polyaxial screw and a plurality of cutouts to accommodate the first elongated spinal rod, a first clamp having a first spherical pocket to receive the first ball spring collar of the cross bar and a first locking means tightened over the first clamp placed above the first collet head. The first locking means enables a snap-fit engagement of the first connector with the first end of the cross bar and the anchor head. Similarly, the second connector includes a second collet head having a recess to receive an anchor head of the second polyaxial screw and a plurality of cutouts to accommodate the second elongated spinal rod, a second clamp having a second spherical pocket to receive the second ball spring collar of the cross bar, a second locking means tightened over the second clamp placed above the second collet head. The second locking means enables a snap-fit engagement of the second connector with the second end of the cross bar and the anchor head.

The first clamp is attached to the first ball spring collar at the first end of the cross bar and the second clamp is attached to the second ball spring collar at the second end of the cross bar. The first and second spherical pockets receive the first and second ball collars and permit the cross bar to translate in either direction for adjusting to the distance and allow rotational adjustment in the axial plane on both sides of a spinal construct.

The cross bar has the first end that is surrounded with the first ball spring collar and the second end that is surrounded with the second ball spring collar. The first ball spring collar and the second ball spring collar attached on the cross bar allows rotational adjustment to the first and second connectors in an axial plane, the rotational adjustment provides stability to the cross-connector when one polyaxial screw is positioned deeper than the other polyaxial screw on the vertebral bodies. The cross bar translates through the first and second spherical pockets through a conical passage which permits the cross bar to be angularly adjusted relative to the first and second clamps.

A portion of the occipital plate member is configured to contact the occipital bone on the region of a human skull and another portion of the occipital plate member is configured to extend from the occipital plate member to an area that is adjacent to at least one vertebra. The pair of elongated spinal rods is then secured to the occipital plate member. The rods are then extended along the posterior aspects of the patient's cervical and potentially thoracic spine on either side of the spinous processes for a desired distance. Once the rod has been secured to the occipital plate member and polyaxial screws, cross connectors may then be employed to maintain the spinal rods at a desired distance from one another.

An eyelet connector, an adjustable angle occipital rod, a side-loading laminar hook, a facet spacer and an adjustable offset rod-to-rod connector are the forming part of the posterior cervical fixation system. The eyelet connector comprises a rod-receiving element with an open side to allow for rod fixation to the occiput bone. The eyelet connector is fixed to the skull with a bone screw inserted through a screw hole and into an occiput. The adjustable angle occipital rod comprises a first rod portion and a second rod portion which pivot in relation to each other about a hinge. The adjustable angle occipital rod further includes a locking mechanism that includes a first disc and a second disc coupled to the first rod portion and the second rod portion respectively utilizing a set screw. In one embodiment, the set screw has a ratcheted surface which engages a ratcheting washer within a set screw housing of the second rod portion. The side-loading laminar hook includes a hook portion which is dimensioned to hook onto a lamina of a cervical vertebra. The facet spacer is dimensioned to be inserted into a facet joint of a vertebra.

In one embodiment, the first and second elongated spinal rods connected to each other with an adjustable offset rod-to-rod connector. The adjustable offset rod-to-rod connector includes a male portion and a female portion that are coupled such that the portions may rotate with respect to each other. Each portion includes a hole for receiving a rod therethrough and a set screw for locking the adjustable offset rod-to-rod connector to the rods.

A multi-load polyaxial screw driver having a handle, a distal end, an outer shaft, a slot for cartridge tab and an inner shaft can be utilized as a storage compartment for polyaxial screws. The outer shaft of the driver can accommodate a plurality of polyaxial screws in tulip heads with a cartridge coupled to each polyaxial screw.

These and other advantages and features of the present embodiment are described with specificity so as to make the present embodiment understandable to one of ordinary skill in the art.

BRIEF DESCRIPTION OF THE DRAWINGS

Many advantages of the present embodiment will be apparent to those skilled in the art with a reading of this specification in conjunction with the attached drawings, wherein like reference numerals are applied to like elements and wherein.

DETAILED DESCRIPTION

Illustrative embodiments are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fixation system disclosed herein boasts a variety of inventive features and components that warrant patent protection, both individually and in combination.

Figure 1:
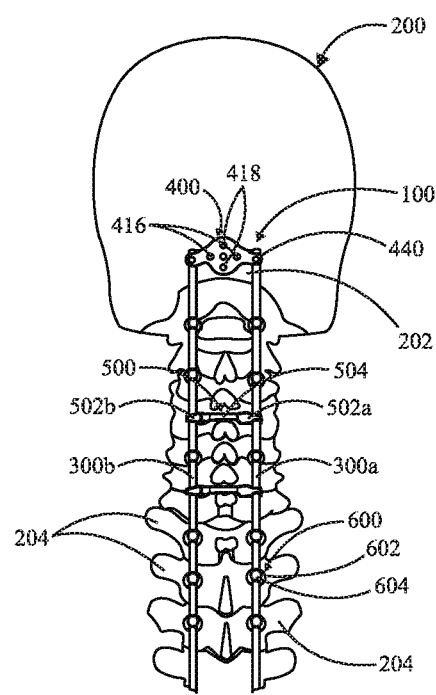
FIG. 1 is a perspective view of an example of a posterior cervical fixation system installed in a spine/skull according to the present embodiment.

FIG. 1 illustrates an example of a posterior cervical fixation system 100 installed in a spine/skull 200 according to the present embodiment. The posterior cervical fixation system 100 comprises a pair of elongated spinal rods 300a, 300b, an occipital plate member 400, a cross connector 500 and a plurality of polyaxial screws 600. The posterior cervical fixation system 100 described herein is for attachment to the posterior part of the human spine from the occiput to the cervical and/or thoracic vertebrae. The posterior cervical fixation system 100 facilitates securing of an orthopedic rod to the spine/skull 200.

The occipital plate member 400 is configured for fixing to an occipital bone 202. The occipital plate member 400 includes at least one aperture 416, 418 (FIG. 2) that receives at least one bone anchor member (not shown) to secure the occipital plate member 400 to the occipital bone 202 and a pair of rod clamping elements 440a, 440b (FIG. 2) dimensioned to receive the first and second elongated spinal rods 300a, 300b respectively. The at least one bone anchor member (not shown) may be at least one of a bone screw, nail, pin or hook. Each polyaxial screw 600 includes an anchor head 602 associated with a fastening member (not shown). The pair of elongated spinal rods includes a first elongated spinal rod 300a and a second elongated spinal rod 300b which is configured to extend along vertebral bodies 204 between the occipital plate member 400 and at least one polyaxial screw 600. The first elongated spinal rod 300a may be of different diameter than the second elongated spinal rod 300b.

Figure 5:
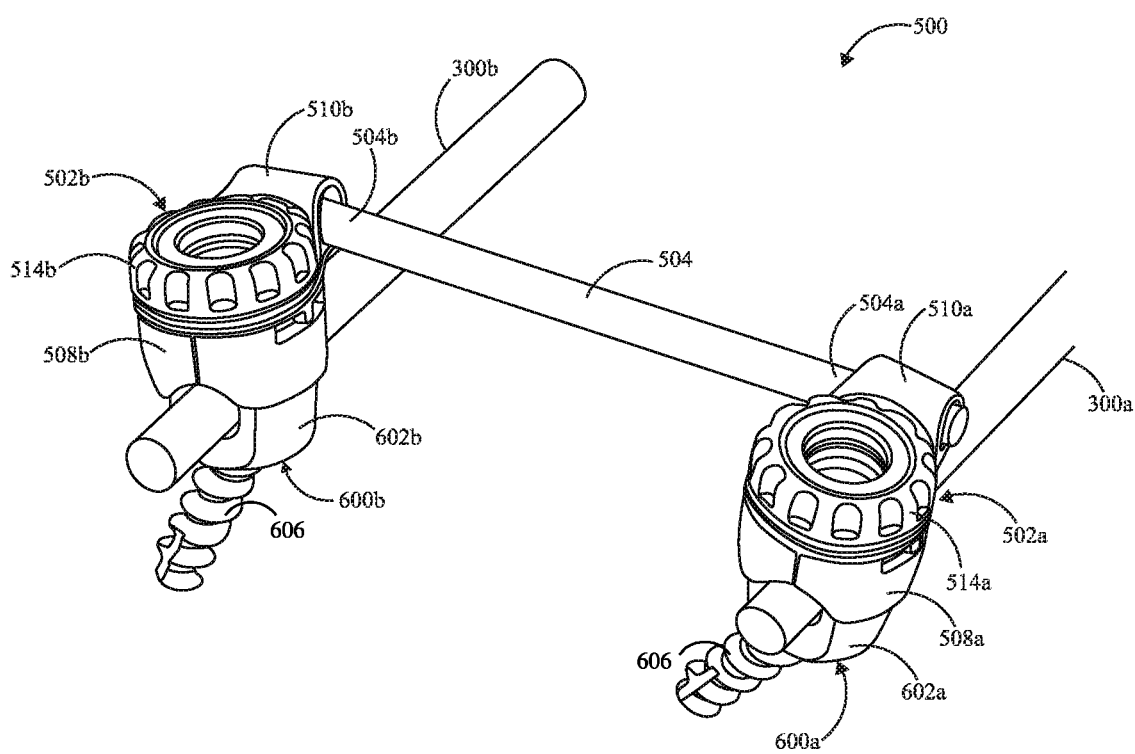
FIG. 5 is a perspective view of a cross connector engaged with the pair of elongated spinal rods forming part of the posterior cervical fixation system of FIG. 1.

The cross connector 500 secures the first and second elongated spinal rods 300a, 300b to the vertebral bodies 204 of the spine. The cross connector 500 includes a pair of collet connectors 502a, 502b (FIG. 5) and a cross bar 504 which is configured to secure the first and second elongated spinal rods 300a, 300b in desired distance. The fastening member 606 of the polyaxial screw 600 is inserted in the vertebral bodies 204 by facing the anchor head 602 upwards to receive the first and second elongated spinal rods 300a, 300b. The first and second elongated spinal rods 300a, 300b are effectively locked in the anchor head 602 by connecting the cross connector 500 to the anchor head 602. The anchor head 602 may include a recess 604 that is adapted to cooperate with a driver (not shown) used to lock the fastening member 606 of the polyaxial screw 600 into the vertebral bodies 204. By way of example only, the recess 604 is shown as a hex-head shaped recess for receiving a hex-head driver. The anchor head 602 is generally spherical in shape and dimensioned to engage with the cross connector 500. Although shown and described by way of example as a polyaxial screw 600, it is including but not limited to a screw, nail, hook, pin, staple, tack, and/or suture. Any or all of these elements may be made of a biologically inert material; preferably any metal customarily used for surgical devices, such as for example titanium or stainless steel.

Figure 2:
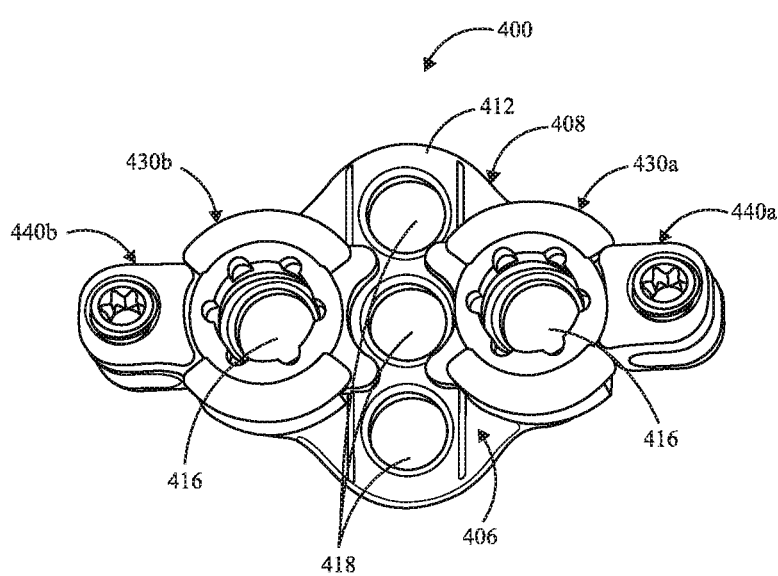
FIG. 2 is a front perspective view of an occipital plate member forming part of the posterior cervical fixation system of FIG. 1 in a collapsed state.
Figure 3:
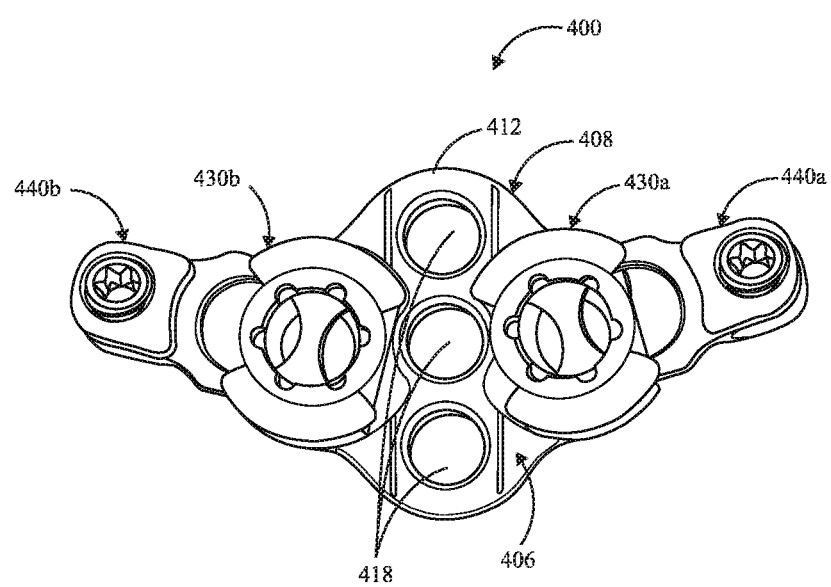
FIG. 3 is a front perspective view of an occipital plate member forming part of the posterior cervical fixation system of FIG. 1 in an expanded state.
Figure 4:
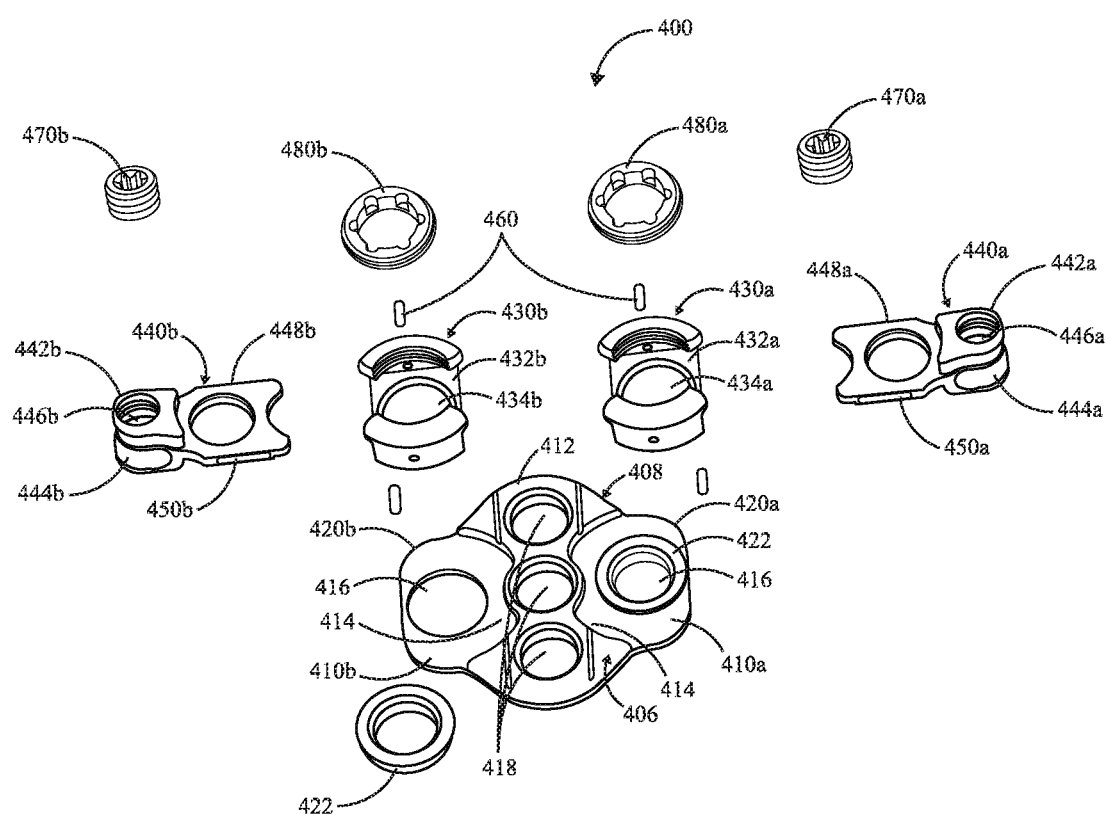
FIG. 4 is an exploded view of the occipital plate member of FIG. 2.

Referring to FIGS. 2-4, the occipital plate member 400 of the posterior cervical fixation system 100 comprises an upper surface 406 and a lower surface (not shown), in which the lower surface (not shown) is configured to contact a portion of the occipital bone 202. The occipital plate member 400 includes a generally flat main body portion 408 having a first surface 410a, a second surface 410b and a centerline axis 412. Both first and second surfaces 410a, 410b have a recessed portion 414 and an opening 416 and the centerline axis 412 has a plurality of openings 418. As an example, the occipital plate member 400 shown in FIGS. 2-4 are provided with five openings, with three of the openings 418 aligned along the centerline axis 412 and additional two openings 416 on either first and second surfaces 410a, 410b of the main body portion 408. These openings 416, 418 may extend through the occipital plate member 400 at an angle such that the bone anchor members (not shown) are guided into the occipital bone 202 at an oblique angle to the transverse axis of the occipital plate member 400. The main body portion 408 further includes a first end 420a in which at least a portion of the first end 420a extends away from the centerline axis 412 and a second end 420b in which at least a portion of the second end 420b extends away from the centerline axis 412. The occipital plate member 400 is fixed to the occipital bone 202 by inserting a plurality of bone anchor members (not shown) through the plurality of openings 418 in the centerline axis and each opening 416 on the first and second surfaces 410a, 410b of the main body portion 408.

The openings 416 on the first and second surfaces 410a, 410b are fitted with a washer 422 that interfaces with the occipital plate member 400 and the bone anchor member (not shown). The occipital plate member 400 further includes a first rotating housing 430a having a lower portion 432a and a hole 434a adaptable to engage with the recessed portion 414 and the opening 416 of the first surface 410a, a second rotating housing 430b having a lower portion 432b and a hole 434b adaptable to engage with the recessed portion 414 and the opening 416 of the second surface 410b. The first and second housings 430a, 430b are able to freely rotate within the recessed portions of the first and second surfaces until a locking means 480a, 480b is deployed to lock the rotating housings 430a, 430b in a desired position.

The occipital plate member 400 further includes a first rod clamping element 440a and a second rod clamping element 440b. The first rod clamping element 440a is dimensioned to couple the occipital plate member 400 to a first elongated spinal rod 300a. Similarly, the second rod clamping element 440b is dimensioned to couple the occipital plate member 400 to a second elongated spinal rod 300b. The first rod clamping element 440a extends laterally from the first end 420a of the main body portion 408 and the second rod clamping element 440b extends laterally from the second end 420b of the main body portion 408. The first rod clamping element 440a includes a first clamp portion 442a having a rod receiving end 444a and a hole 446a extending therethrough in communication with the rod receiving end 444a and a first body portion 448a having a pin slot 450a therethrough on a body of the first body portion 448a. Similarly, the second rod clamping element 440b includes a second clamp portion 442b having a rod receiving end 444b and a hole 446b extending therethrough in communication with the rod receiving end 444b and a second body portion 448b having a pin slot 450b therethrough on a body of the second body portion 448b.

The occipital plate member 400 further includes a plurality of pins 460 that is coupled to the first and second rotating housings 430a, 430b. The pin slots 450a, 450b of the first and second rod clamping elements 440a, 440b receive the pins 460 and enable each of the rod clamping elements 440a, 440b to translate medially and laterally within each of the rotating housings 430a, 430b to achieve a collapsed state (FIG. 2) and an expanded state (FIG. 3). The occipital plate member 400 further includes a first locking element 470a to lock the first elongated spinal rod 300a within the rod receiving end 444a of the first rod clamping element 440a and a second locking element 470b to lock the second elongated spinal rod 300b within the rod receiving end 444b of the second rod clamping element 440b. The first and second locking elements 470a, 470b may comprise, for example, a set screw. According to the embodiment shown in FIGS. 2-4, in order to achieve this locking interaction, the set screws 470a, 470b threadedly engage the holes 446a, 446b on the first and second clamp portions 442a, 442b such that the set screws 470a, 470b may be advanced toward the elongated spinal rods 300a, 300b until a distal tip of the set screws 470a, 470b contacts the elongated spinal rods 300a, 300b. A first locking means 480a engages the first rotating housing 430a and the first rod clamping element 440a to the first surface 410a of the main body portion 408 and a second locking means 480b engages the second rotating housing 430b and the second rod clamping element 440b to the second surface 410b of the main body portion 408. According to the exemplary embodiment shown in FIGS. 2-4, both the locking means 480a, 480b comprise a lock nut which is dimensioned to lock the first and second rotating housings 430a, 430b and the first and second rod clamping elements 440a, 440b with the first and second surfaces 410a, 410b of the main body portion 408 when the first and second rotating housings 430a, 430b and first and second rod clamping elements 440a, 440b are in a desired position.

The first and second rod clamping elements 440a, 440b have a generally C-shaped rod-receiving ends 450a, 450b for facilitating the side-loading of the first and second elongated spinal rods 300a, 300b therethrough. The occipital plate member 400 may be provided in any size suitable for any particular patient. The bone anchor members (not shown) may be provided having any diameter and length dimension suitable for implantation into a patient's skull.

Figure 6:
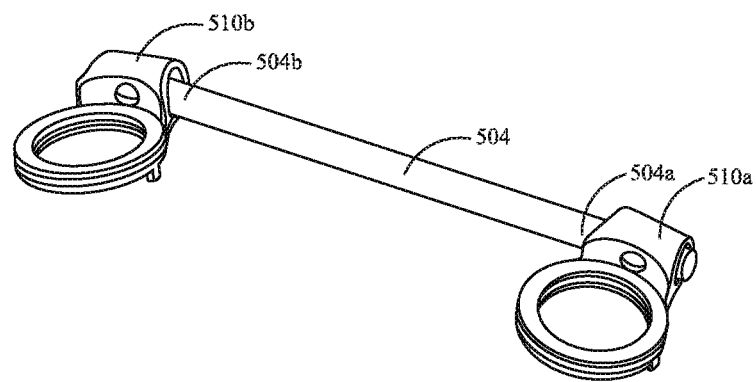
FIG. 6 is a perspective view of a cross bar engaged with a first clamp and a second clamp on either end thereof forming part of the cross connector of FIG. 5.
Figure 7:
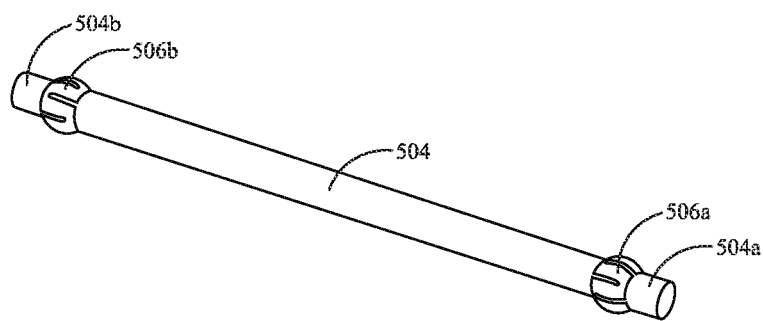
FIG. 7 is a perspective view of a cross bar surrounded with a pair of ball spring collar forming part of the cross connector of FIG. 5.

FIGS. 5-9 illustrate one of embodiment of a cross connector 500 and its associated components forming part of a posterior cervical fixation system 100. The cross connector 500 further includes a first connector 502a, a second connector 502b and a cross bar 504. The cross bar 504 includes a first end 504a that is surrounded with a first ball spring collar 506a (FIG. 7) and a second end 504b that is surrounded with a second ball spring collar 506b (FIG. 7). The first connector 502a is configured to receive the first elongated spinal rod 300a and adaptable to directly attach with a first polyaxial screw 600a. Similarly, the second connector 502b is configured to receive a second elongated spinal rod 300b and adaptable to directly attach with a second polyaxial screw 600b.

The first connector 502a includes a first collet head 508a having a recess (not shown) to receive an anchor head 602a of the first polyaxial screw 600a and a plurality of cutouts (not shown) to accommodate the first elongated spinal rod 300a, a first clamp 510a having a first spherical pocket 512a to receive the first ball spring collar 506a of the cross bar 504 and a first locking means 514a tightened over the first clamp 510a placed above the first collet head 508a. The first locking means 514a enables a snap-fit engagement of the first connector 502a with the first end 504a of the cross bar 504 and the anchor head 602a. Similarly, the second connector 502b includes a second collet head 508b having a recess (not shown) to receive an anchor head 602b of the second polyaxial screw 600b and a plurality of cutouts (not shown) to accommodate the second elongated spinal rod 300b, a second clamp 510b having a second spherical pocket 512b to receive the second ball spring collar 506b of the cross bar 504, a second locking means 514b tightened over the second clamp 510b placed above the second collet head 508b. The second locking means 514b enables a snap-fit engagement of the second connector 502b with the second end 504b of the cross bar 504 and the anchor head 602b.

As shown in FIG. 6, the first clamp 510a attached to the first ball spring collar 506a at the first end 504a of the cross bar 504 and the second clamp 510a attached to the second ball spring collar 506b at the second end 504b of the cross bar 504. The first and second spherical pockets 512a, 512b receive the first and second ball collars 506a, 506b and permit the cross bar 504 to translate in either direction for adjusting to the distance and allow rotational adjustment in the axial plane on both sides of a spinal construct.

Figures 8A, 8B:
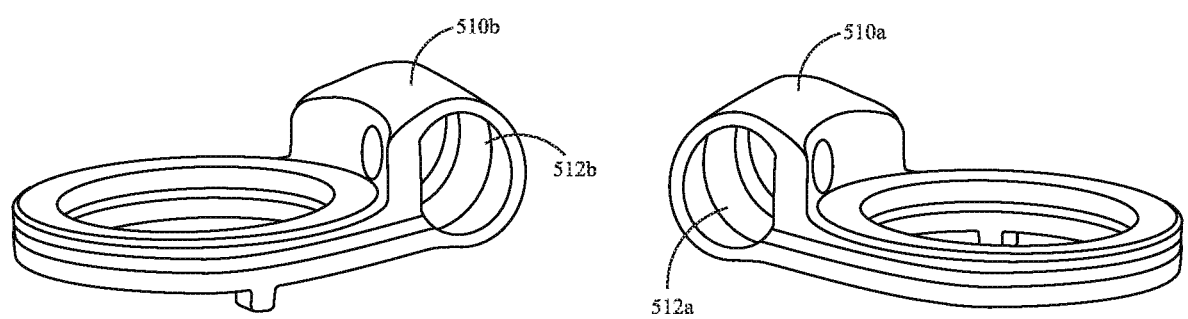
FIG. 8A is a side perspective view of a first clamp of FIG. 6.
FIG. 8B is a side perspective view of a second clamp of FIG. 6.
Figure 9:
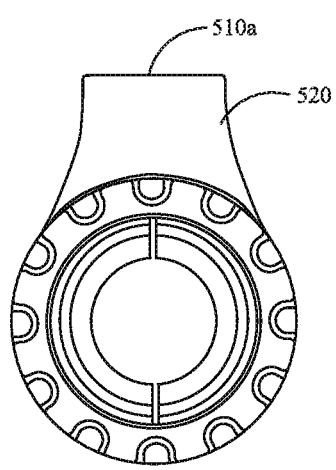
FIG. 9 is a plan view of a clamp of FIG. 6.

As shown in FIG. 7, the cross bar 504 has the first end 504a that is surrounded with the first ball spring collar 506a and the second end 504b that is surrounded with the second ball spring collar 506b. The first and the second ball spring collars 506a, 506b attached on the cross bar 504 allows rotational adjustment to the first and second connectors 502a, 502b in an axial plane, the rotational adjustment provides stability to the cross-connector 500 when one polyaxial screw 600a is positioned deeper than the other polyaxial screw 600b on the vertebral bodies. As shown in FIGS. 8A-9, the cross bar 504 translates through the first and second spherical pockets 512a, 512b through a conical passage 520. The conical passage 520 is larger than the diameter of the cross bar 504 and permits the cross bar 504 to be angularly adjusted relative to the first and second clamps 510a, 510b. The cross bar 500 may be provided in any length suitable for extending between the first and second elongated spinal rods 300a, 300b.

The elongated spinal rods 300a, 300b extend along the posterior aspects of the patient's cervical and potentially thoracic spine on either side of the spinous processes for a desired distance. Any combination of anchor elements, including polyaxial screws and/or laminar hooks as described above may be used to secure the rods to the cervical and/or thoracic vertebrae. Any combination of anchor elements, including bone anchors and/or locking screws as described above may be used to secure the occipital plate to the occipital bone 202. Once the elongated spinal rods 300a, 300b have been secured to the occipital plate member 400 and polyaxial screws 600, cross connectors 500 may then be employed to maintain the elongated spinal rods 300a, 300b at a desired distance from one another.

Figure 10:
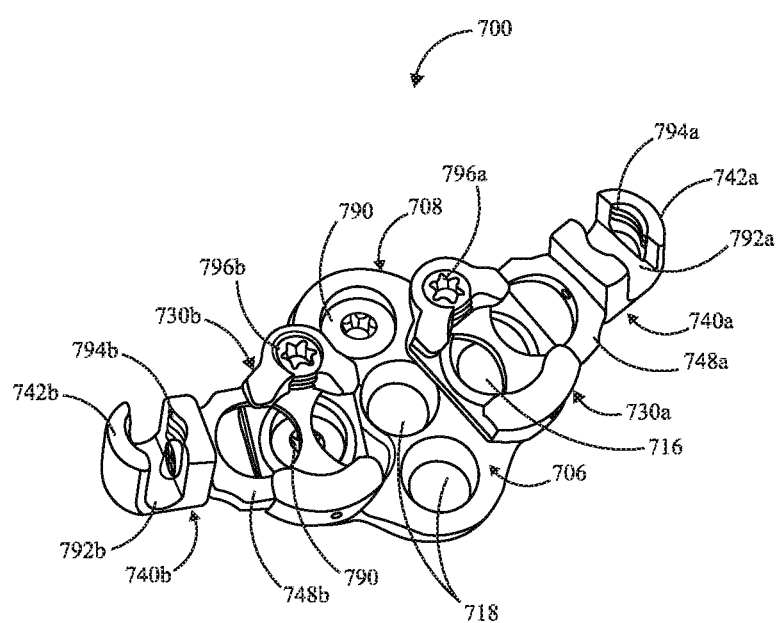
FIG. 10 is a top perspective view of an alternate embodiment of the occipital plate member of FIG. 4 in an expanded state.
Figure 11:
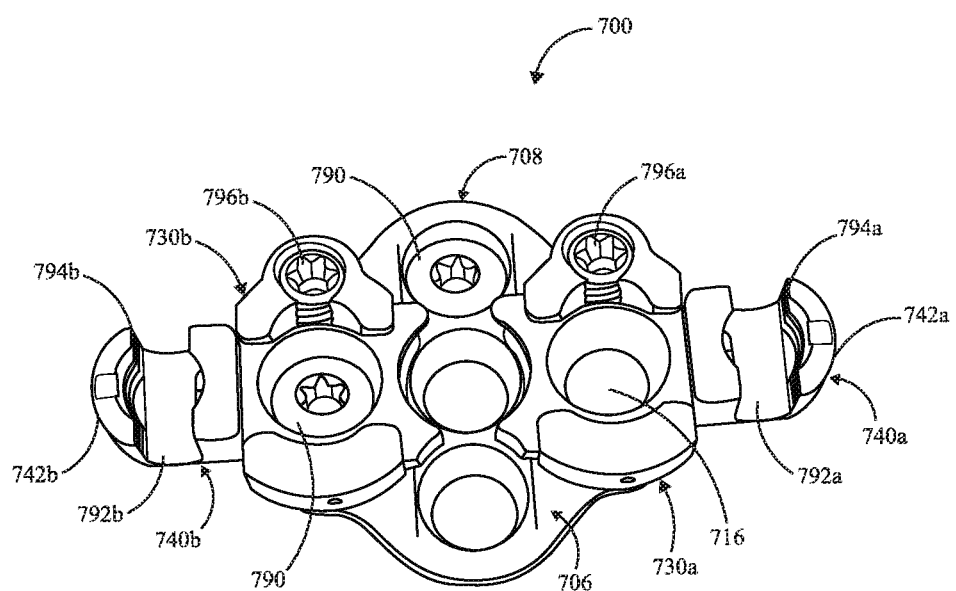
FIG. 11 is a top perspective view of an alternate embodiment of the occipital plate member of FIG. 4 in a collapsed state.

FIGS. 10 and 11 illustrate an alternative embodiment of the occipital plate of FIG. 2. FIG. 10 depicts an occipital plate member attached with U-shaped rod receiving elements in its expanded state. FIG. 11 depicts an occipital plate member attached with U-shaped rod receiving elements in its collapsed state. The occipital plate member 700 in this embodiment is similar structurally and functionally to the embodiment described above, with a difference in that the first and second rod clamping elements 740a, 740b have a generally U-shaped rod-receiving ends 792a, 792b with a threaded side walls 794a, 794b extending therethrough in communication with the rod receiving ends 792a, 792b respectively, in which the rod receiving ends 792a, 792b are dimensioned to face upward. Also, a first locking means 796a and a second locking means 796b are locking screws which are positioned vertically offset from center of a first rotating housing 730a and a second rotating housing 730b respectively. The first and second locking means 796a, 796b enables the locking of the first rod clamping element 740a and the second rod clamping element 740b with the first and second rotating housings 730a, 730b in a desired position. The openings 716, 718 in the main body portion 708 are angled such that the bone anchor members 790 are guided into the occipital bone 202 at an oblique angle to the transverse axis of the occipital plate member 700. More particularly, the illustrated embodiment is similar in all other respects to the preferred embodiment described above, and as such similar components and features are numbered similarly, except in the 700s rather than the 400s.

The occipital plate member 700 has an upper surface 706 and a lower surface (not shown), in which the lower surface (not shown) is configured to contact a portion of the occipital bone 202. The occipital plate member 700 includes a main body portion 708 having a first surface, a second surface and a centerline axis. Both the first and second surfaces have a recessed portion and an opening 716 and the centerline axis has a plurality of openings 718. The main body portion 708 further includes a first end and a second end, in which at least a portion of the first and second ends extends away from the centerline axis. The occipital plate member 700 is fixed to the occipital bone 202 by inserting a plurality of bone anchor members 790 through the plurality of openings 718 in the centerline axis and the opening 716 on the first and second surfaces of the main body portion 708.

The occipital plate member 700 further includes a first rotating housing 730a having a lower portion and a hole adaptable to engage with the recessed portion and the opening 716 of the first surface of the main body portion 708, and a second rotating housing 730b having a lower portion and a hole adaptable to engage with the recessed portion and the opening 716 of the second surface of the main body portion 708. The first and second housings 730a, 730b are able to freely rotate within the recessed portions of the first and second surfaces until a locking means 796a, 796b is deployed to lock the rotating housings 730a, 730b in a desired position.

The occipital plate member 700 further includes a first rod clamping element 740a and a second rod clamping element 740b. The first rod clamping element 740a is dimensioned to couple the occipital plate member 700 to the first elongated spinal rod 300a. Similarly, the second rod clamping element 740b is dimensioned to couple the occipital plate member 700 to the second elongated spinal rod 300b. The first and second rod clamping elements 740a, 740b extend laterally from the first end and second end of the main body portion 708 respectively. The first rod clamping element 740a includes a first clamp portion 742a having the rod receiving end 792a and the threaded side wall 794a extending therethrough in communication with the rod receiving end 792a and a first body portion 748a having a pin slot therethrough on a body of the first body portion 748a. Similarly, the second rod clamping element 740b includes a second clamp portion 742b having the rod receiving end 792b and the threaded side wall 794b extending therethrough in communication with the rod receiving end 792a and a second body portion 748b having a pin slot therethrough on a body of the second body portion 748b.

The occipital plate member 700 further includes a plurality of pins coupled to the first and second rotating housings 730a, 730b. The pin slots of first and second rod clamping elements 740a, 740b receive the pins and enable the first and second rod clamping elements 740a, 740b to translate medially and laterally within the first and second rotating housings 730a, 730b to achieve a collapsed state (FIG. 11) and an expanded state (FIG. 10 The occipital plate member 700 further includes a first locking element (not shown) to lock the first elongated spinal rod 300a within the rod receiving end 744a of the first rod clamping element 740a and a second locking element (not shown) to lock the second elongated spinal rod 300b within the rod receiving end 744b of the second rod clamping element 740b. The first and second locking elements (not shown) may comprise, for example, a set screw.

The first locking means 796a engages the first rotating housing 730a and the first rod clamping element 740a to the main body portion 708 and the second locking means 796b engages the second rotating housing 730b and the second rod clamping element 740b to the main body portion 708. Deploying the first and second locking means 796a, 796b urges the rotating housings 730a, 730b against the top surface 706 of the plate, thereby locking the rotating housings 730a, 730b and rod clamping elements 740a, 740b in a desired position.

Figure 12:
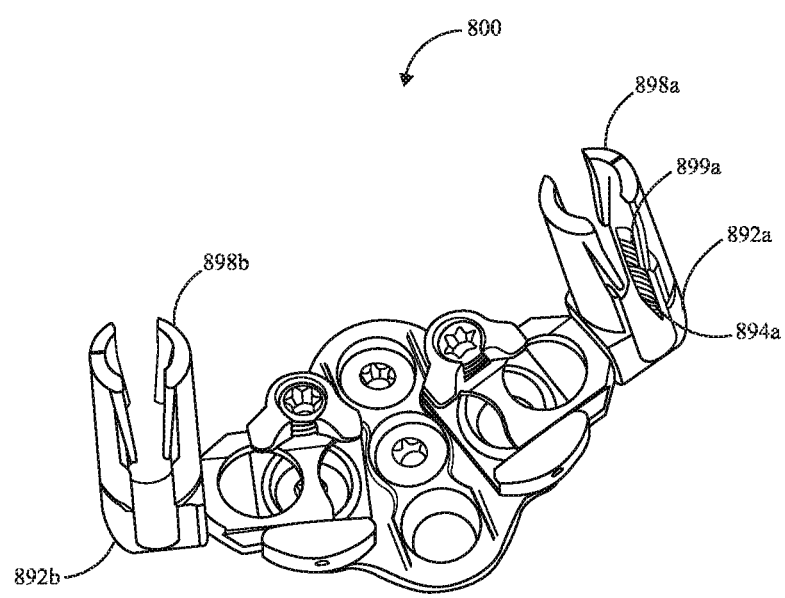
FIG. 12 is a top perspective view of an alternate embodiment of the occipital plate member of FIG. 10.
Figure 13:
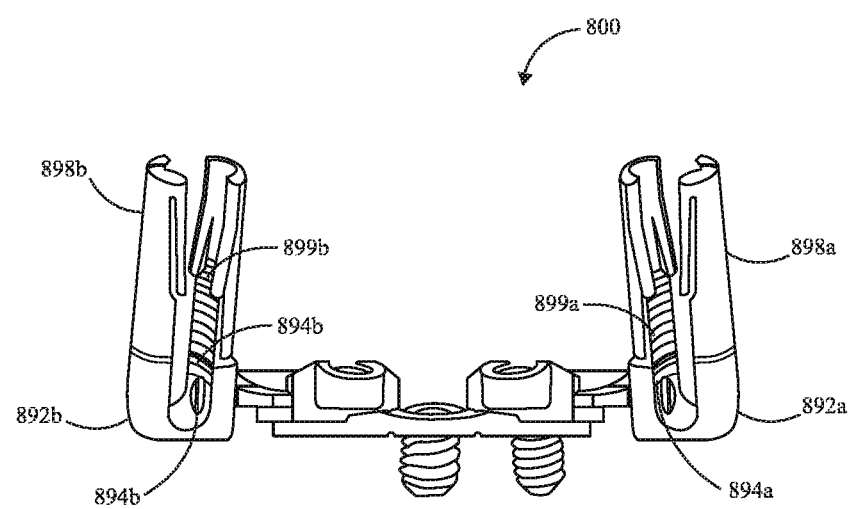
FIG. 13 is a side perspective view of an alternate embodiment of the occipital plate member of FIG. 11.

FIGS. 12 and 13 illustrate an alternative embodiment of the occipital plate member of FIGS. 10 and 11 in an expanded state and a collapsed state. The occipital plate member 800 in this embodiment is similar structurally and functionally to the embodiment described above, with a difference in that the U-shaped rod-receiving ends 892a, 892b with a threaded side walls 894a, 894b extending therethrough in communication with the rod receiving ends 892a, 892b that is attached with rod receiving towers 898a, 898b having a threaded side walls 899a, 899b extending therethrough in communication with the rod receiving towers 898a, 898b. More particularly, the illustrated embodiment is similar in all other respects to the embodiment in FIGS. 10 and 11, and as such similar components and features are numbered similarly, except in the 800s rather than the 700s.

Figure 14:
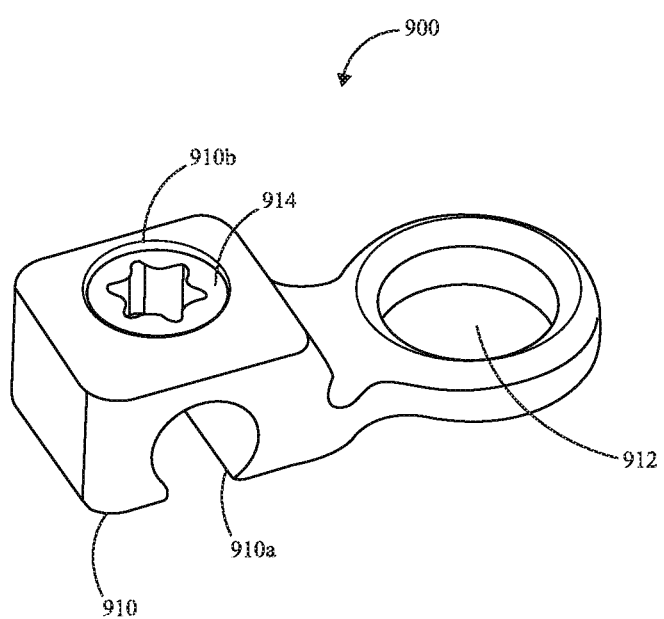
FIG. 14 is a perspective view of an eyelet connector forming part of the posterior cervical fixation system of FIG. 1 for fixing a spinal rod to human occiput.

FIG. 14 illustrates one example of an eyelet connector 900 forming part of the posterior cervical fixation system 100. The eyelet connector 900 is provided for fixing the elongated spinal rods 300a, 300b to human occiput. The eyelet connector 900 comprises a rod receiving element 910 and a screw hole 912. The rod receiving element 910 having an open side 910a facing the occipital bone that allows the elongated spinal rods 300a, 300b to pass through and a set screw hole 910b for the spinal rod fixation to the occiput with a minimal profile. The elongated spinal rods 300a, 300b are locked with the occipital bone 202 by inserting a set screw 914 through the set screw hole 910b. The eyelet connector 900 is fixed to the skull with a bone screw (not shown) inserted through the screw hole 912 and into the occiput.

Figure 15:
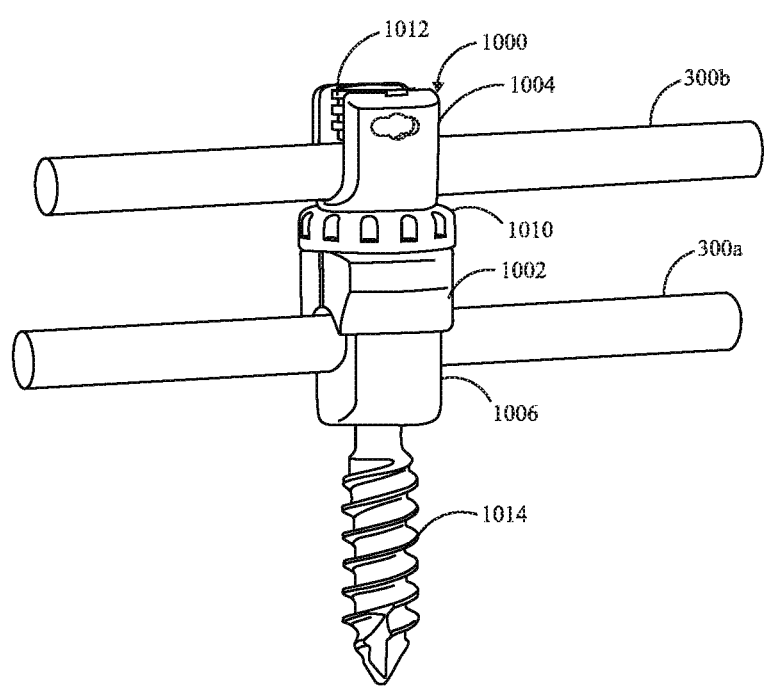
FIG. 15 is a perspective view of an example of a collet and anchor head connector forming part of a posterior cervical fixation system of FIG. 1 for top loading a second spinal rod.
Figure 16:
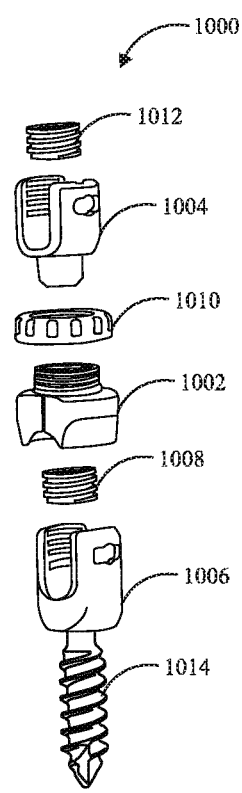
FIG. 16 is an exploded perspective view of a collet and anchor head connector of FIG. 15.

FIGS. 15 and 16 illustrate an example of a collet and anchor head connector 1000 forming part of a posterior cervical fixation system for top loading a second elongated spinal rod. The collet and anchor head connector 1000 is engaged with a first elongated spinal rod 300a and top loaded with a second elongated spinal rod 300b as shown in FIG. 15. In each of the presented embodiments, the second elongated spinal rod 300b is shown as co-linear with the first elongated spinal rod 300a. The first and second elongated spinal rods 300a, 300b are secured into the bone with a cross connector 500 and an occipital plate member 400 (FIGS. 1 and 10). According to this example, shown in FIGS. 15 and 16, a collet connector 1002 and a second anchor head 1004 may also be oriented to allow the second elongated spinal rod 300b to be positioned transverse to the first elongated spinal rod 300a. The collet connector 1002 may be coupled to a first anchor head 1006 with a first set screw 1008 and a locking cap 1010 is threaded onto the collet connector 1002. The first set screw 1008 is received within apertures (not shown) in the collet connector 1002 and the locking cap 1010. The second elongated spinal rod 300b may be secured within the second anchor head 1004 with a second set screw 1012. The second anchor head 1004 is inserted into the locking cap 1010 and engaged with the collet connector 1002. A screw shank 1014 attached with the first anchor head 1006 is inserted into the bone.

Figure 17:
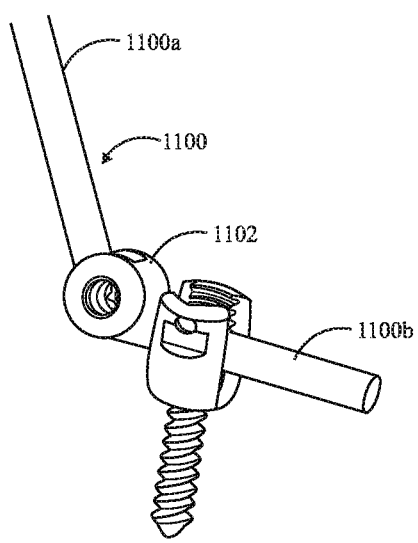
FIG. 17 is a perspective view of an adjustable angle occipital rod attached to a polyaxial screw forming part of the posterior cervical fixation system of FIG. 1.
Figure 18:
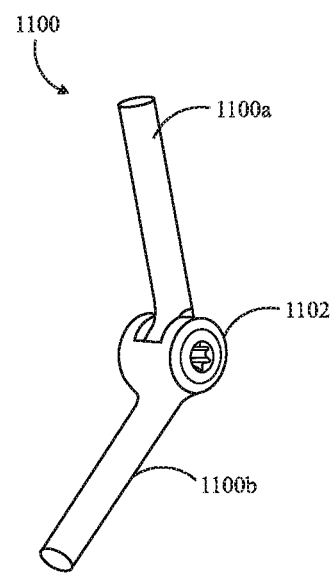
FIG. 18 is a perspective view of the adjustable angle occipital rod of FIG. 17.
Figure 19A:
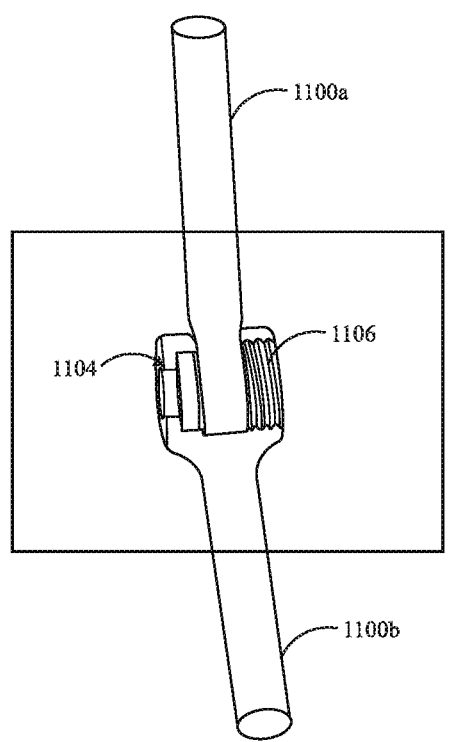
FIG. 19A is a partial sectional view of the adjustable angle occipital rod of FIG. 17, detailing a locking mechanism.
Figure 19B:
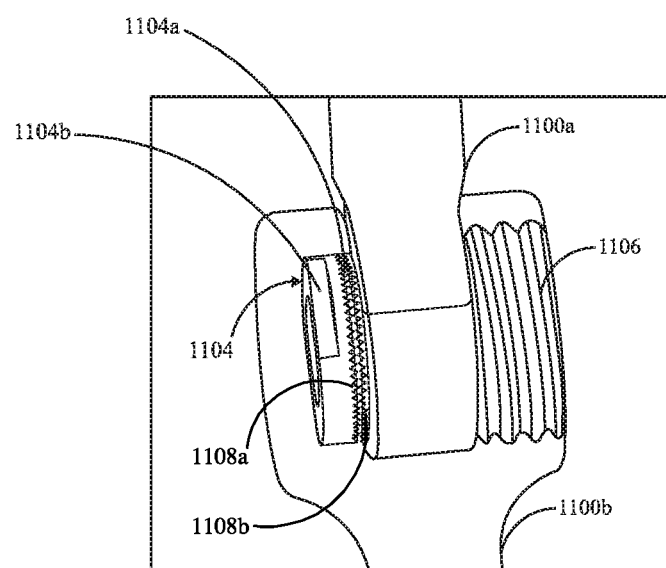
FIG. 19B is a sectional close-up view of the locking mechanism in the adjustable angle occipital rod according to FIG. 19A.

FIGS. 17-19B illustrate an adjustable angle occipital rod forming part of a posterior cervical fixation system of FIG. 1. FIG. 17 depicts an adjustable angle occipital rod attached to a polyaxial screw. FIG. 18 depicts an adjustable angle occipital rod illustrating a hinge. FIGS. 19A and 19B depict an adjustable angle occipital rod that includes a locking mechanism. The adjustable angle occipital rod 1100 comprises a first rod portion 1100a and a second rod portion 1100b that pivot in relation to each other about a hinge 1102. The first and second rods 1100a, 1100b further comprises a locking mechanism 1104 therebetween. The locking mechanism 1104 includes a first disc 1104a coupled to the first rod portion 1100a and a second disc 1104b coupled to the second rod portion 1100b. The first and second discs 1104a, 1104b have an engagement surface (1108a) that faces the engagement surface (1108b) of the other disc, the engagement surfaces 1108a, 1108b having a plurality of teeth to allow the first and second rods 1100a, 1100b to be rotated and locked in discrete increments of angulation relative to each other. The first and second rod portions 1100a, 1100b are engaged together with a set screw 1106. When the set screw 1106 is in the unlocked position, the first and second rod portions 1100a, 1100b can rotate freely about the hinge 1002. When the first and second rod portions 1100a, 1100b are in the desired position, the set screw 1106 can be turned to the locked position, urging the engagement surfaces 1108a, 1108b of the first and second discs 1104a, 1104b in contact with each other to prevent movement of the first and second rod portions 1100a, 1100b.

Figure 20:
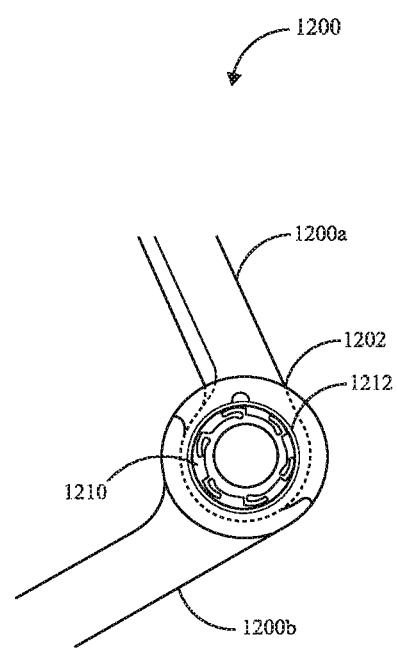
FIG. 20 is a partial sectional view of an alternate embodiment of an adjustable angle occipital rod of FIG. 19A, detailing a set screw housing.
Figure 21:
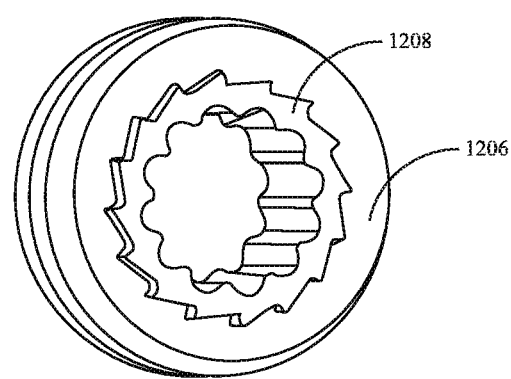
FIG. 21 is an enlarged view of a set screw forming part of an adjustable angle occipital rod of FIG. 20.

FIGS. 20 and 21 illustrate an alternative embodiment of an adjustable angle occipital rod of FIGS. 17-19B. FIG. 20 depicts an adjustable angle occipital rod attached with screw housing. FIG. 21 depicts a set screw forming part of an adjustable angle occipital rod of FIG. 20. The adjustable angle occipital rod 1200 in this embodiment is similar structurally and functionally to the embodiment described above, with a difference in that a first rod portion 1200a and a second rod portion 1200b that pivot in relation to each other about a hinge 1202. The set screw 1206 has a ratcheted surface 1208 that engages a ratcheting washer 1210 is secured within set screw housing 1212 of the second rod portion 1200b. The interaction of the ratcheting surface 1208 on the set screw 1206 with the ratcheting washer 1210 limits the turning and tightening of the set screw 1206 to only one direction. More particularly, the illustrated embodiment is similar in all other respects to the preferred embodiment described above, and as such similar components and features are numbered similarly, except in the 1200s rather than the 1100s.

Figure 22:
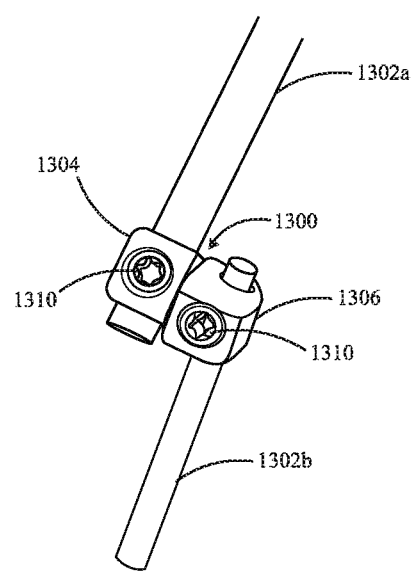
FIG. 22 is a perspective view of an adjustable offset rod-to-rod connector engaged with a pair of elongated spinal rods forming part of the posterior cervical fixation system of FIG. 1.
Figure 23A:
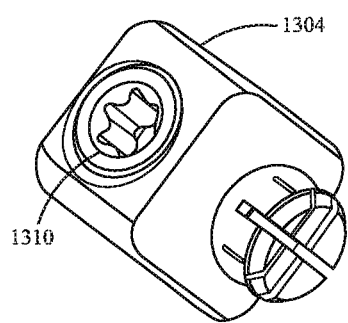
FIG. 23A is a perspective view of a male portion forming part of the adjustable offset rod-to-rod connector of FIG. 22.
Figure 23B:
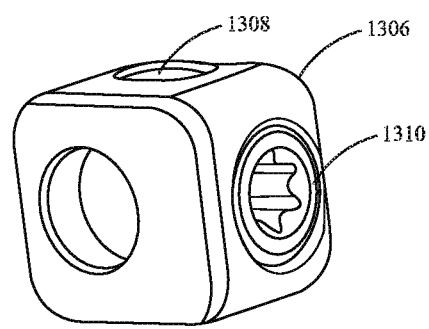
FIG. 23B is a perspective view of a female portion forming part of the adjustable offset rod-to-rod connector of FIG. 22.

FIGS. 22-23B demonstrate one embodiment of an adjustable offset rod-to-rod connector. FIG. 22 depicts the adjustable offset rod-to-rod connector engaged with a pair of elongated spinal rods. FIG. 23A depicts a male portion forming part of the adjustable offset rod-to-rod connector of FIG. 22. FIG. 23B depicts a female portion forming part of the adjustable offset rod-to-rod connector of FIG. 22. The adjustable offset rod-to-rod connector 1300 facilitates the adjacent engagement of a first elongated spinal rod 1302a and a second elongated spinal rod 1302b. The adjustable offset rod-to-rod connector 1300 includes a male portion 1304 and a female portion 1306 that are coupled such that the male and female portions 1304, 1306 may rotate with respect to each other. The male and female portions 1304, 1306 include a rod receiving hole 1308 for receiving the rods 1302a, 1302b therethrough and a set screw 1310 for locking the adjustable offset rod-to-rod connector 1300 to the rods 1302a, 1302b.

Figure 24:
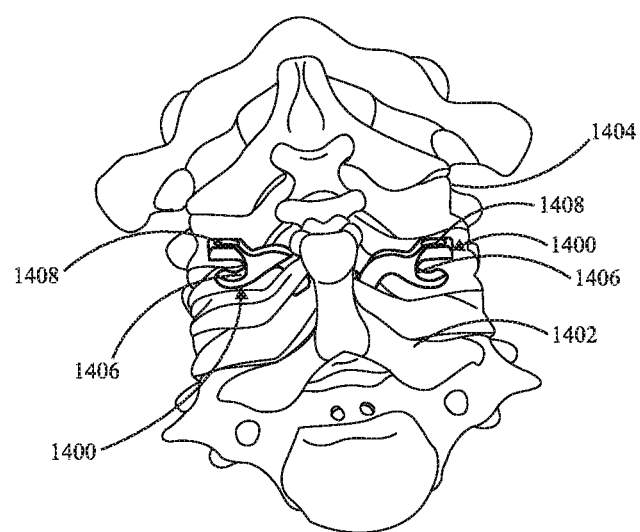
FIG. 24 is a perspective view of a side-loading laminar hook placed onto a lamina of a cervical vertebra forming part of a posterior cervical fixation system of FIG. 1.
Figure 25:
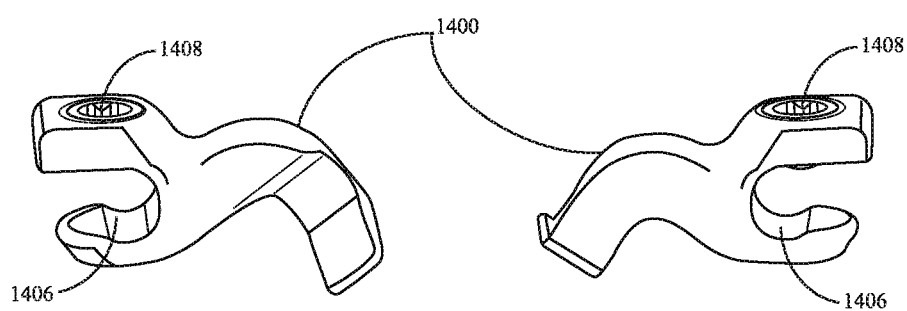
FIG. 25 is a side perspective view of a side-loading laminar hook of FIG. 24.
Figure 26:
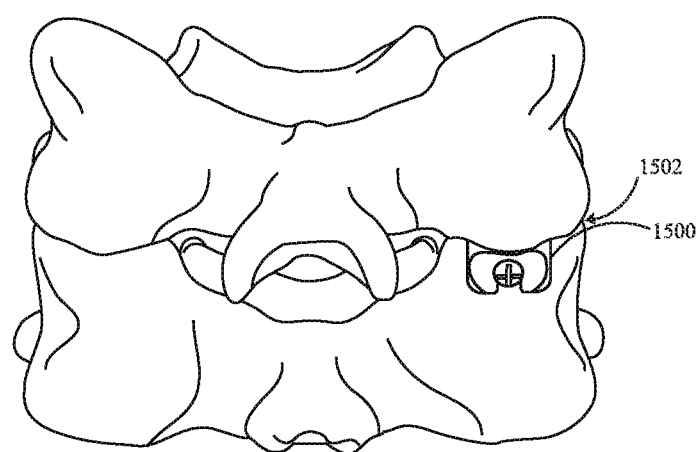
FIGS. 26 and 27 are perspective views of a facet spacer placed within a facet joint forming part of a posterior cervical fixation system of FIG. 1.
Figure 27:
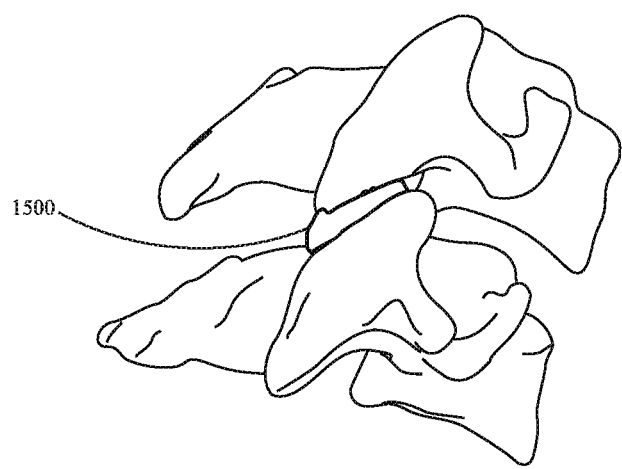
Figure 28:
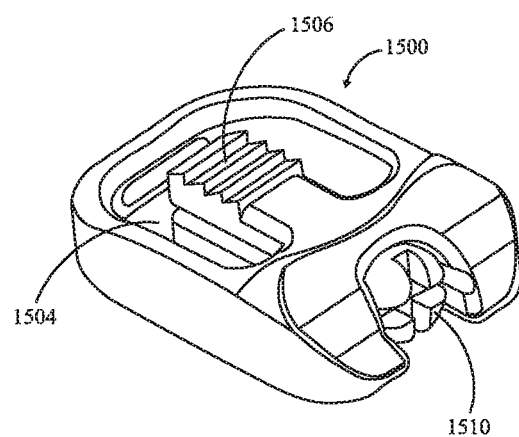
FIGS. 28-30 are front and perspective views, respectively, of the facet spacer of FIGS. 26 and 27, illustrating particularly a graft window, a deformable tab and a locking screw aperture.
Figure 29:
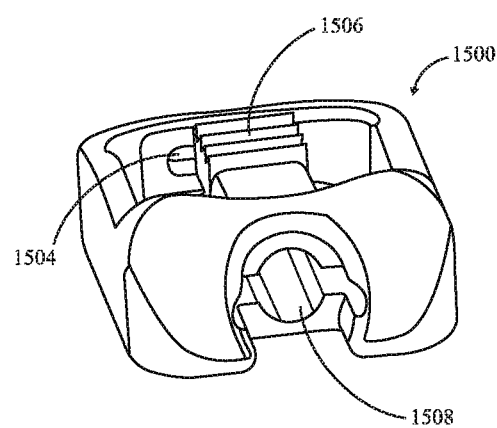

FIGS. 24 and 25 demonstrate one embodiment of a side-loading laminar hook forming part of a posterior cervical fixation system of FIG. 1. The side-loading laminar hook 1400 is dimensioned to hook onto a lamina 1402 of a cervical vertebra 1404. The side-loading laminar hook 1400 has a generally C-shaped rod-receiving portion 1406 for receiving spinal rods (not shown) therethrough. The first and second elongated spinal rods (not shown) are locked in place within the rod-receiving portion 1406 by a set screw 1408.

Figure 30:
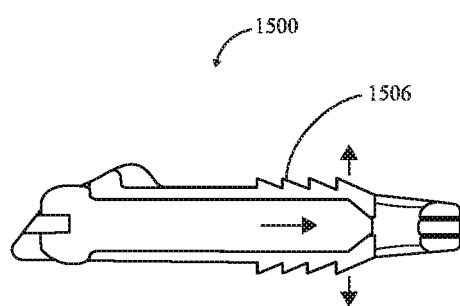

FIGS. 26-30 demonstrate one embodiment of a facet spacer forming part of a posterior cervical fixation system of FIG. 1. The facet spacer 1500 is dimensioned to be inserted into a facet joint 1502 of a vertebra. The facet spacer 1500 includes a graft window 1504 to allow bone growth therethrough to achieve fusion of the facet joint 1502 and a plurality of deformable tabs 1506 extending into the graft window 1504. The plurality of deformable tabs 1506 further includes teeth, which will engage the facet spacer 1500. The facet spacer 1500 includes a locking screw aperture 1508 for receiving a locking screw 1510. When the locking screw 1510 is inserted into the locking screw aperture 1508 of the facet spacer 1500, the plurality of deformable tabs 1506 urges apart (FIG. 30).

Figure 31:
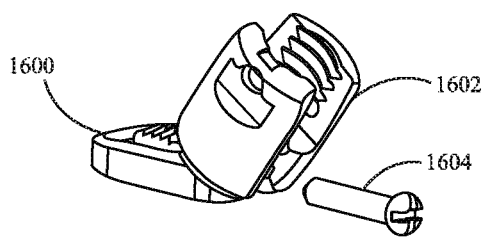
FIG. 31 is a perspective view of an alternative embodiment of the facet spacer of FIGS. 28-30.

FIG. 31 illustrates one embodiment of the facet spacer of FIGS. 26-30. The facet spacer 1600 in this embodiment is similar structurally and functionally to the embodiment described above in FIGS. 26-30, with a difference in that an anchor head 1602 is coupled to the facet spacer 1600. The anchor head 1602 is capable of receiving a spinal rod (not shown). The anchor head 1602 is attached to a locking screw 1604 which allows the adjustment of the position of the anchor head 1602 to a desired position for receiving the spinal rod (not shown). More particularly, the illustrated embodiment is similar in all other respects to the preferred embodiment described above, and as such similar components and features are numbered similarly, except in the 1600s rather than the 1500s.

Figure 32:
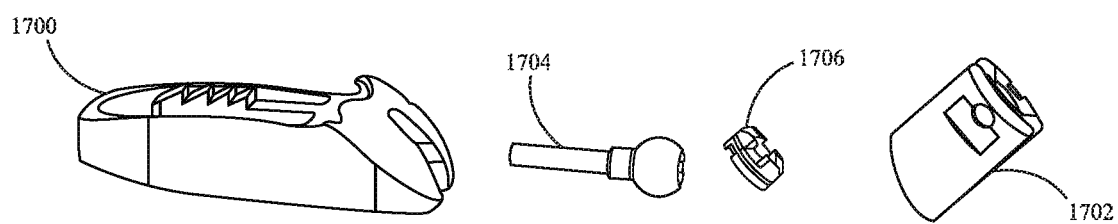
FIG. 32 is a perspective view of another embodiment of the facet spacer of FIGS. 28-30.

FIG. 32 illustrates yet another embodiment of the facet spacer of FIGS. 26-30. The facet spacer 1700 in this embodiment is similar structurally and functionally to the embodiment described above in FIGS. 26-30, with a difference in that an anchor head 1702 is attached to a locking screw 1704 that is having a spherical head 1706, allowing for adjustment of the position of the anchor head 1702 to a desired position for receiving a spinal rod (not shown). More particularly, the illustrated embodiment is similar in all other respects to the preferred embodiment described above, and as such similar components and features are numbered similarly, except in the 1700s rather than the 1600s.

Figure 33:
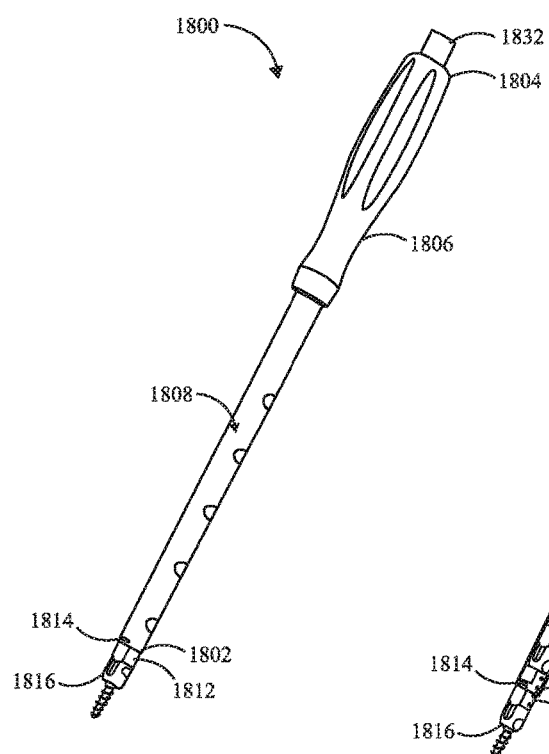
FIG. 33 is a perspective view of one embodiment of a multi-load polyaxial screw driver, illustrating particularly an outer shaft accommodated with a plurality of polyaxial screws with a cartridge coupled to each polyaxial screw.
Figure 34:
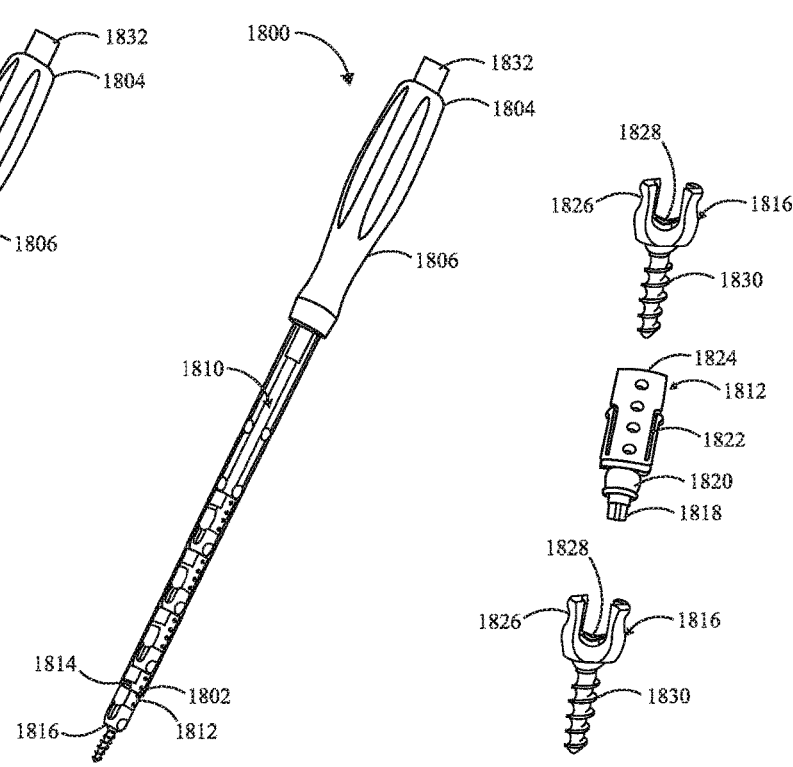
FIG. 34 is a perspective view of the multi-load polyaxial screw driver, of FIG. 33, illustrating particularly an inner shaft drives the plurality of screws and cartridge toward a distal end of the driver.
Figure 35:
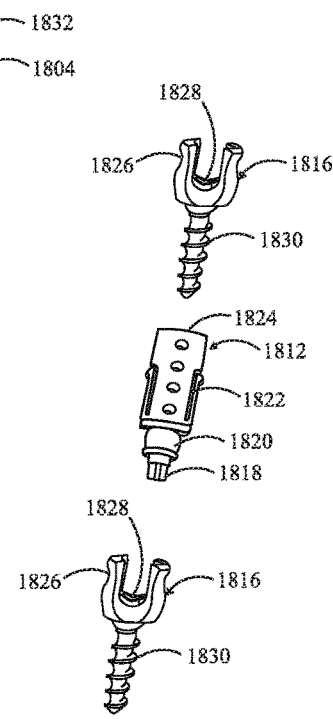
FIG. 35 is an assembling view of polyaxial screws with cartridge forming part of the multi-load polyaxial screw driver of FIG. 33.

FIGS. 33-35 demonstrate one embodiment of a multi-load polyaxial screw driver. The multi-load polyaxial screw driver 1800 having a distal end 1802 and a proximal end 1804. The multi-load polyaxial screw driver 1800 includes a handle 1806, an outer shaft 1808, inner shaft 1810, cartridge 1812 and slots for cartridge tab 1814. The outer shaft 1808 of the multi-load polyaxial screw driver 1800 can accommodate a plurality of polyaxial screws 1816. The cartridge 1812 include a hex-shaped end 1818 to mate to a hex-shaped recess 1828 in the anchor head 1826 of the polyaxial screw 1816 and a spherical tip 1820 proximal to the hex-shaped end 1818 that will engage the inside the hex-shaped recess 1828 of the anchor head 1826. Although shown as having a hex-shaped head in the exemplary embodiment, it will be appreciated that the cartridge may have a shaped end to complement the shape of any anchor head with which the multi-load polyaxial screw driver is used. The cartridge 1812 is coupled to each polyaxial screw 1816. The hex shaped end 1818 of the cartridge 1812 is engaged in the anchor head 1826 of one polyaxial screw 1816 and a screw shank 1830 of other polyaxial screw 1816 is engaged with a head 1824 of the cartridge 1812 and so on in a nested fashion. The cartridges 1812 further include side tabs 1822 that will engage slots 1814 in the outer shaft 1808 of the driver 1800 when the cartridge 1812 has been advanced to the distal end 1802 of the driver 1800 and the polyaxial screw engaged with that cartridge is exposed distally to the multi-load screwdriver. After the exposed polyaxial screw is deployed into the vertebral bone, the corresponding cartridge 1812 can then be pinched in at the side tabs 1822 and the empty cartridge 1812 along is released from the driver 1800. The cartridge 1812 can be removed from the outer shaft 1808 of the driver 1800 once the polyaxial screw 1816 has been driven into and secured in the spine. The head 1824 of the cartridge 1812 includes an aperture (not shown) for receiving the screw shank 1830 of the next polyaxial screw 1816. The inner shaft 1810 of the driver 1800 is spring-loaded which urges the plurality of polyaxial screws 1816 and the cartridges 1812 toward the distal end 1802 of the driver 1800.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A cross connector of a posterior cervical fixation system, the cross connector comprising:
    a first connector comprising a first collet head, a first recess to receive an anchor head of a first bone fastener, one or more first cutouts to receive a first elongate spinal rod therethrough, a first clamp with a first spherical pocket, and a first locknut;
    a second connector comprising a second collet head, a second recess to receive the anchor head of a second bone fastener, one or more second cutouts to receive a second elongate spinal rod therethrough, a second clamp with a second spherical pocket, and a second locknut; and
    a cross bar that connects the first connector and the second connector and secures the first and second elongate spinal rods to vertebral bodies of a spine and by a pre-determined distance to each other, the cross bar having a first end surrounded with a first ball spring collar and a second end surrounded with a second ball spring collar,
    wherein the first spherical pocket receives the first ball spring collar therewithin and allows rotation of the first connector in an axial plane of the system, and
    wherein the first locknut is configured to allow snap-fit engagement of the first connector with the anchor head of the first bone fastener and the first end of the cross bar.

2. The cross connector of claim 1, wherein the first connector further comprises a first conical passage at least partially surrounding the first spherical pocket.

3. The cross connector of claim 2, wherein the first conical passage permits the cross bar to be angularly adjusted relative to the first clamp.

4. The cross connector of claim 1, wherein the first connector is configured to lock the first elongate spinal rod in the anchor head of the first bone fastener by connecting the first connector to the anchor head.

5. The cross connector of claim 1, wherein the first clamp includes a first portion placed above the first collet head, and the first locknut tightens over the first portion of the first clamp thereby locking the first end of the cross bar to the first clamp.

6. The cross connector of claim 1, wherein the first clamp includes a second portion attached to the first portion and housing the first spherical pocket therewithin, the second portion located on a side of the first collet head, and wherein the first spherical pocket comprises an inner spherical surface.

7. The cross connector of claim 1, wherein the first or second bone fastener is a polyaxial screw.

8. The cross connector of claim 1, wherein the first spherical pocket allows the cross bar to translate therethrough thereby reaching the pre-determined distance between the first and second elongate spinal rods prior to locking the cross bar to the first connector.

9. The cross connector of claim 1, wherein the first and second elongate spinal rods are configured to extend along posterior aspects of the spine lateral to spinous processes.

10. The cross connector of claim 1, is configured to be installed on the first and second bone fasteners after the first and second bone fasteners are secured to the vertebral bodies and the first and second elongate spinal rods are received in the anchor head of the first and second bone fasteners.

11. The cross connector of claim 1, wherein the rotation of the first connector in an axial plane of the system provides stability to the cross connector when the first bone fastener is positioned deeper than the second bone fastener in the vertebral bodies.

12. A cross connector of a posterior cervical fixation system, the cross connector comprising:
- a first connector comprising a first collet head, a first recess to receive an anchor head of a first bone fastener, one or more first cutouts to receive a first elongate spinal rod therethrough, a first clamp with a first spherical pocket, a first conical passage at least partially surrounding the first spherical pockets, and a first locknut;
- a second connector comprising a second collet head, a second recess to receive the anchor head of a second bone fastener, one or more second cutouts to receive a second elongate spinal rod therethrough, and a second clamp with a second spherical pocket, and a second locknut; and
- a cross bar that secures the first and second elongate spinal rods to vertebral bodies of a spine and by a pre-determined distance to each other, the cross bar having a first end surrounded with a first ball spring collar and a second end surrounded with a second ball spring collar,
- wherein the first spherical pocket receives the first ball spring collar therewithin and allows rotation of the first connector in an axial plane of the system, and wherein the first conical passage permits the cross bar to be angularly adjusted relative to the first clamp, and
- wherein the first locknut is configured to allow snap-fit engagement of the first connector with the anchor head of the first bone fastener and the first end of the cross bar.

13. The cross connector of claim 12, wherein the first connector is configured to lock the first elongate spinal rod in the anchor head of the first bone fastener by connecting the first connector to the anchor head.

14. The cross connector of claim 12, wherein the first clamp includes a first portion placed above the first collet head, and the first locknut tightens over the first portion of the first clamp thereby locking the first end of the cross bar to the first clamp.

15. The cross connector of claim 12, wherein the first clamp includes a second portion attached to the first portion and housing the first spherical pocket therewithin, the second portion located on a side of the first collet head, and wherein the first spherical pocket comprises an inner spherical surface.

16. The cross connector of claim 12, wherein the first spherical pocket allows the cross bar to translate therethrough thereby reaching the pre-determined distance between the first and second elongate spinal rods prior to locking the cross bar to the first connector.

17. The cross connector of claim 12, wherein the first and second elongate spinal is configured to extend along posterior aspects of the spine lateral to spinous processes.

18. A cross connector of a posterior cervical fixation system, the cross connector comprising:
- a first connector comprising a first collet head to receive an anchor head of a first bone fastener from a bottom thereof and to receive a first elongate spinal rod therethrough, a first clamp with a first spherical pocket, a first conical passage at least partially surrounding the first spherical pockets, and a first locknut;
- a second connector configured to receive an anchor head of a second bone fastener and a second elongate spinal rod; and
- a cross bar that secures the first and second elongate spinal rods to vertebral bodies and by a pre-determined distance to each other, the cross bar having a first end surrounded with a first ball spring collar and a second end surrounded with a second ball spring collar,
- wherein the first spherical pocket receives the first ball spring collar therewithin and allows rotation of the first connector in an axial plane of the system, and wherein the first and second elongate spinal rods are configured to extend along posterior aspects of the spine lateral to spinous processes, and
- wherein the first locknut is configured to allow snap-fit engagement of the first connector with the anchor head of the first bone fastener and the first end of the cross bar.

* * * * *